(12) United States Patent
Zhang et al.

(10) Patent No.: US 7,319,152 B2
(45) Date of Patent: Jan. 15, 2008

(54) 5-ARYL-INDAN-1-ONE AND ANALOGS USEFUL AS PROGESTERONE RECEPTOR MODULATORS

(75) Inventors: Puwen Zhang, Audubon, PA (US); Jeffrey Curtis Kern, Gilbertsville, PA (US); Eugene Anthony Terefenko, Center Valley, PA (US); Eugene John Trybulski, Huntingdon Valley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/522,862

(22) Filed: Sep. 18, 2006

(65) Prior Publication Data

US 2007/0066675 A1   Mar. 22, 2007

Related U.S. Application Data

(60) Provisional application No. 60/718,355, filed on Sep. 19, 2005.

(51) Int. Cl.
C07D 207/30 (2006.01)
C07D 263/30 (2006.01)
C07D 261/06 (2006.01)
C07D 333/08 (2006.01)

(52) U.S. Cl. ............ 548/562; 548/235; 548/247; 549/78

(58) Field of Classification Search ........ 548/562
See application file for complete search history.

(56) References Cited

U.S. PATENT DOCUMENTS

| | | | |
|---|---|---|---|
| 5,329,050 | A | 7/1994 | Weisse et al. |
| 5,360,936 | A | 11/1994 | Weisse et al. |
| 5,578,646 | A | 11/1996 | Pineyro-Lopez |
| 5,719,136 | A | 2/1998 | Chwalisz et al. |
| 6,288,126 | B1 | 9/2001 | LeSuisse et al. |
| 6,355,648 | B1 | 3/2002 | Fensome et al. |
| 6,391,907 | B1 | 5/2002 | Fensome et al. |
| 6,436,929 | B1 | 8/2002 | Zhang et al. |
| 6,509,334 | B1 | 1/2003 | Zhang et al. |
| 6,521,657 | B2 | 2/2003 | Fensome et al. |
| 6,566,358 | B2 | 5/2003 | Zhang et al. |
| 6,583,145 | B1 | 6/2003 | Fensome et al. |
| 6,608,068 | B2 | 8/2003 | Fensome et al. |
| 6,713,478 | B2 | 3/2004 | Zhang et al. |
| 6,841,568 | B2 | 1/2005 | Fensome et al. |
| 6,946,454 | B2 | 9/2005 | Fensome et al. |
| 7,081,457 | B2 | 7/2006 | Zhang et al. |
| 7,084,168 | B2 | 8/2006 | Fensome et al. |
| 7,091,234 | B2 | 8/2006 | Fensome et al. |
| 2004/0186101 | A1 | 9/2004 | Zhang et al. |
| 2005/0085470 | A1 | 4/2005 | Zhang et al. |
| 2005/0171186 | A1 | 8/2005 | Fensome et al. |
| 2006/0030615 | A1 | 2/2006 | Fensome et al. |
| 2006/0142280 | A1 | 6/2006 | Zhang et al. |
| 2006/0160882 | A1 | 7/2006 | Fensome et al. |

FOREIGN PATENT DOCUMENTS

| | | |
|---|---|---|
| EP | 467407 | 11/1995 |
| EP | 0568879 | 7/1996 |
| EP | 587107 | 8/1996 |

(Continued)

OTHER PUBLICATIONS

Horwitz et al, Progestins, Progesterone Receptors, and Breast Cancer, Hormones and Cancer, 283-306, 1996.

(Continued)

*Primary Examiner*—Rebecca Anderson
*Assistant Examiner*—Shawquia Young
(74) *Attorney, Agent, or Firm*—Howson & Howson LLP; Arnold S. Milowsky

(57) ABSTRACT

Compounds of formula I or II are provided, wherein $R_1$-$R_8$ are defined herein, and pharmaceutical compositions and kits containing these compounds. Also provided are methods of inducing contraception, providing hormone replacement therapy, treating cycle-related symptoms, or treating or preventing benign or malignant neoplastic disease using the compounds of formula I, formula II, or formula III, wherein $R_1$-$R_9$ are defined herein:

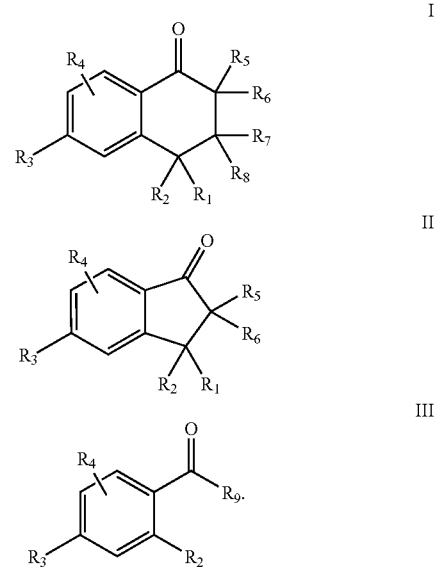

3 Claims, No Drawings

FOREIGN PATENT DOCUMENTS

| | | |
|---|---|---|
| EP | 1175397 | 8/2004 |
| FR | 2 705 671 | 2/1994 |
| WO | WO 97/27846 | 7/1997 |
| WO | WO 98/13061 | 4/1998 |
| WO | WO 98/22436 | 5/1998 |
| WO | WO 98/44797 | 10/1998 |
| WO | WO 98/09940 | 12/1998 |
| WO | WO 99/18079 | 4/1999 |
| WO | WO 99/61413 | 12/1999 |
| WO | WO 00/37433 | 6/2000 |
| WO | WO 00/66554 A1 | 11/2000 |
| WO | WO 00/66555 | 11/2000 |
| WO | WO 00/66556 | 11/2000 |
| WO | WO 00/66570 A1 | 11/2000 |
| WO | WO 00/66571 A1 | 11/2000 |
| WO | WO 00/78724 | 12/2000 |
| WO | WO 03/091225 | 11/2003 |
| WO | WO 2006/023107 A1 | 3/2006 |

OTHER PUBLICATIONS

Kekkonen et al, Sequential Regimen of the Antiprogesterone RU486 and Synthetic Progestin for Contraception, Fertility and Sterility, vol. 60, No. 4, (Oct. 1993).

Kettel et al, Endocrine Responses to Long-term Administration of the Antiprogesterone RU486 in Patients with Pelvic Endometriosis, Fertility and Sterility, vol. 56, No. 3, (Sep. 1991).

Mangelsdorf et al, The Nuclear Receptor Superfamily: The Second Decade, Cell, vol. 83, 835-839, (Dec. 15, 1995).

Michna et al, Differentiation Therapy with Progesterone Antagonists, Ann. N.Y. Acad. Sci. 761, 224, (1995).

Murphy et al, Regression of Uterine Leiomyomata in Response to the Antiprogesterone RU 486, Journal of Clinical Endocrinology and Metabolism, vol. 76, No. 2, 513-517, (1993).

Ulmann et al, Clinical Uses of Mifepristone (MFP), Ann. N.Y. Acad. Sci. 261, 248, (1995).

5-ARYL-INDAN-1-ONE AND ANALOGS USEFUL AS PROGESTERONE RECEPTOR MODULATORS

CROSS-REFERENCE TO RELATED APPLICATIONS

This application claims the benefit under 35 USC 119(e) of prior U.S. Provisional Patent Application No. 60/718,355, filed Sep. 19, 2005.

BACKGROUND OF THE INVENTION

This invention relates to agonists and antagonists of the progesterone receptor, their preparation and utility.

Intracellular receptors (IR) form a class of structurally related gene regulators known as "ligand dependent transcription factors" (Mangelsdorf, D. J. etc. Cell, 83, 835, 1995). The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as PR ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and the protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, either along or in the presence of an ER agonist. ER agonists are used to treat the symptoms of menopause, but have been associated with a proliferative effect on the uterus which can lead to an increased risk of uterine cancers. Co-administration of a PR agonist reduces/ablates that risk.

PR antagonists may also be used in contraception. In this context they may be administered alone (Ulmann, et al., Ann. N.Y. Acad. Sci., 261, 248, 1995), in combination with a PR agonist (Kekkonen, et al, Fertility and Sterility, 60, 610, 1993) or in combination with a partial ER antagonist such as tamoxifen (U.S. Pat. No. 5,719,136).

PR antagonists may also be useful for the treatment of hormone dependent breast cancers (Horwitz, et al, Horm. Cancer, 283, 1996, pub: Birkhaeuser, Boston, Mass., ed. Vedeckis) as well as uterine and ovarian cancers. PR antagonists may also be useful for the treatment of non-malignant chronic conditions such as uterine fibroids (Murphy, et al, J. Clin. Endo. Metab., 76, 513, 1993) and endometriosis (Kettel, et al., Fertility and Sterility, 56, 402, 1991).

PR antagonists may also be useful in hormone replacement therapy for post menopausal patients in combination with a partial ER antagonist such as tamoxifen (U.S. Pat. No. 5,719,136).

PR antagonists, such as mifepristone and onapristone, have been shown to be effective in a model of hormone dependent prostate cancer, which may indicate their utility in the treatment of this condition in men (Michna, et al, Ann. N.Y. Acad. Sci., 761, 224, 1995).

What is needed in the art are alternative progesterone receptor modulators.

SUMMARY OF THE INVENTION

In one aspect, a compound of formula I is provided, wherein $R_1$-$R_8$ are defined below.

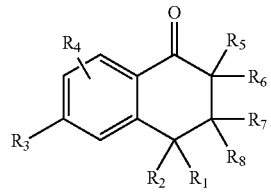

In another aspect, a compound of formula II is provided, wherein $R_1$-$R_6$ are defined below.

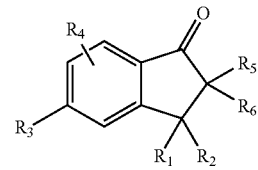

In a further aspect, methods of inducing contraception, providing hormone replacement therapy, treating cycle-related symptoms, or treating or preventing benign or malignant neoplastic disease are provided using compounds of formula I or II.

In yet another aspect, methods of inducing contraception, providing hormone replacement therapy, treating cycle-related symptoms, or treating or preventing benign or malignant neoplastic disease are provided using compounds of formula III, wherein $R_2$-$R_4$ and $R_9$ are defined below:

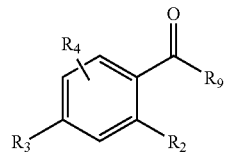

Other aspects and advantages will be readily apparent from the following detailed description of the invention.

DETAILED DESCRIPTION OF THE INVENTION

Novel progesterone receptor (PR) modulators and uses of the same in treating a variety of conditions are provided. The novel compounds have been shown to act as competitive inhibitors of progesterone binding to the PR and act as PR modulators in functional models. These PR modulators are thereby effective as PR agonists or PR antagonists.

As used herein, the terms "anti-progestational agent", "anti-progestin" and "progesterone receptor antagonist" are understood to be synonymous. Similarly, "progestin", "progestational agent", and "progesterone receptor agonist" are understood to refer to compounds of the same activity.

A compound of formula I is provided:

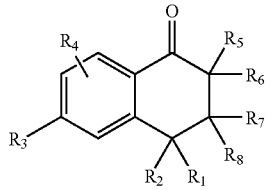

I wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; provided that both $R_1$ and $R_2$ are not H; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i) or (ii): (i) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl; or a pharmaceutically acceptable salt thereof.

A compound of formula II is provided:

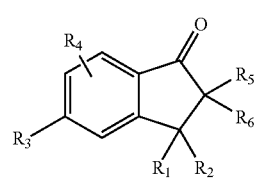

II wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; provided that both $R_1$ and $R_2$ are not H; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is a saturated 5 or 6 membered heteroaryl ring containing in its backbone 1 to 3 heteroatoms selected from among O, S, SO, $SO_2$, and $NR^C$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^CCOR^D$; or $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$ and $R_6$ are, independently, H, F, or $C_1$ to $C_3$ alkyl; or a pharmaceutically acceptable salt thereof.

In one embodiment, in the compound of formula I or II, $R_1$ and $R_2$ are, independently, H or $C_1$ to $C_6$ alkyl; $R_3$ is a 5 membered heteroaryl ring containing in its backbone 1 $NR^C$ heteroatom and substituted with 0 to 3 substituents selected from among H, CN, and $C_1$ to $C_3$ alkyl; $R_4$, $R_5$, $R_6$, $R_7$, and $R_8$ are H.

In another embodiment, in the compound of formula I or II, $R_3$ is 1-methyl-2-cyanopyrrole, 1-methyl-2-cyano-4-acetylpyrrole or 2-chlorothiophene.

In a further embodiment, in the compound of formula I or II, $R_3$ is 1-methyl-2-cyanopyrrole.

In yet another embodiment, in the compound of formula I or II, $R_1$ is heteroaryl or aryl.

In still a further embodiment, in the compound of formula I or II, $R_3$ is of the structure:

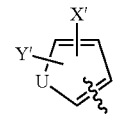

wherein, U is O, S, or $NR^C$; $R^C$ is H, $C_1$ to $C_4$ alkyl, or $COR^D$; $R^D$ is $C_1$ to $C_4$ alkyl; X' is selected from among halogen, CN, $NO_2$, $C_1$ to $C_3$ alkyl, and $C_1$ to $C_3$ alkoxy; and Y' is selected from among H and $C_1$ to $C_4$ alkyl.

In another embodiment, in the compound of formula I or II, $R_3$ is of the structure:

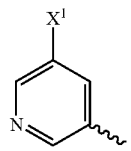

wherein, $X^1$ is halogen, CN, $C_1$ to $C_3$ alkoxy, or $NO_2$.

In still a further embodiment, the compound of formula I is 1-methyl-5-(5-oxo-5,6,7,8-tetrahydronaphthalen-2-yl)-1H-pyrrole-2-carbonitrile.

In yet another embodiment, in the compound of formula I or II, $R_1$ and $R_2$ are fused to form any of rings (a), (b), or (c).

In a further embodiment, the compound of formula II is 5-(3,5-dimethylisoxazol-4-yl)-3,3-dimethylindan-1-one; 1-methyl-5-(3-methyl-1-oxo-2,3-dihydro-1H-inden-5-yl)-1H-pyrrole-2-carbonitrile; 5-(3,3-dimethyl-1-oxo-2,3-dihydro-1H-inden-5-yl)-1-methyl-1H-pyrrole-2-carbonitrile; 1-methyl-5-(1-oxo-2,3-dihydro-1H-inden-5-yl)-1H-pyrrole-2-carbonitrile; 4-acetyl-1-methyl-5-(1-oxo-2,3-dihydro-1H-inden-5-yl)-1H-pyrrole-2-carbonitrile; 5-(3,5-dimethylisoxazol-4-yl)-3,3-dimethylindan-1-one; 5-(5-chlorothien-2-yl)-3,3-dimethylindan-1-one; and 3,3-dimethyl-5-thien-3-yl-indan-1-one, or a pharmaceutically acceptable salt thereof.

The term "alkyl" is used herein to refer to both straight- and branched-chain saturated aliphatic hydrocarbon groups having 1 to about 8 carbon atoms, and desirably 1 to about 6 carbon atoms (i.e., $C_1$, $C_2$, $C_3$, $C_4$, $C_5$ or $C_6$). Similarly, the term "lower alkyl" is used herein to refer to alkyl groups as just described, but having 1 to about 3 carbon atoms. Unless otherwise specified, the alkyl groups are not substituted.

The term "cycloalkyl" is used herein to an alkyl group as just described, but cyclic in structure and having 3 to about 8 carbon atoms. In one embodiment, a cycloalkyl group has 3 to about 8 carbon atoms. In another embodiment, a cycloalkyl group has about 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds and containing about 3 to about 8 carbon atoms. In one embodiment, the term alkenyl refers to an alkyl group having 1 or 2 carbon-carbon double bonds. In a further embodiment, an alkenyl group has about 2 to about 8 carbon atoms. In another embodiment, an alkenyl group has about 2 to about 6 carbon atoms. Unless otherwise specified, the alkenyl groups are not substituted.

The term "alkynyl" is used herein to refer to both straight- and branched-chain alkyl groups having one or more carbon-carbon triple bond and having about 3 to about 8 carbon atoms. In one embodiment, the term alkynyl refers to an alkyl group having 1 or 2 carbon-carbon triple bonds and having about 3 to about 6 carbon atoms. Unless otherwise specified, the alkynyl groups are not substituted.

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic, substituted aryl, substituted heterocyclic, alkoxy, aryloxy, substituted alkoxy, alkylcarbonyl, alkylcarboxy, alkylamino, or arylthio. These substituents may be attached to any carbon of an alkyl, alkenyl, alkynyl or cycloalkyl group provided that the attachment constitutes a stable chemical moiety.

The term "acyl" as used herein refers to a carbonyl substituent, i.e., a C(O)(R) group where R is a straight- or branched-chain hydrocarbon group including, without limitation, alkyl, alkenyl, and alkynyl groups. In one embodiment the R groups have 1 to about 8 carbon atoms, and in a further embodiment 1 to about 6 carbon atoms. The term "substituted acyl" refers to an acyl group which is substituted with 1 or more groups including halogen, CN, OH, and $NO_2$.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl. Desirably, the aryl group is an optionally substituted phenyl group.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkylcarbonyl, alkylcarboxy, alkylamino, and arylthio, which groups can be optionally substituted. Desirably, a substituted aryl group is substituted with 1 to about 4 substituents.

The term "heteroaryl", as used herein, refers to an optionally substituted, mono-, di-, tri-, or other multicyclic aromatic ring system that includes at least one, and desirably from 1 to about 4 heteroatom ring members including sulfur, oxygen and nitrogen. In one embodiment, a heteroaryl group can contain about 3 to about 50 carbon atoms, including all combinations and subcombinations of ranges and specific numbers of carbon atoms therein. In another embodiment, a heteroaryl group can contain about 4 to about 10 carbons. Non-limiting examples of heteroaryl groups include, for example, pyrrolyl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

The term "substituted heteroaryl" refers to an heteroaryl group which is substituted with one or more substituents including halogen, CN, OH, $NO_2$, amino, alkyl, cycloalkyl, alkenyl, alkynyl, alkoxy.

The term "heterocyclic" as used herein refers to a stable 4- to 7-membered monocyclic or multicyclic heterocyclic ring which is saturated or partially unsaturated. The heterocyclic ring has in its backbone carbon atoms and one or more heteroatoms including nitrogen, oxygen, and sulfur atoms. Desirably, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. The heterocyclic groups are selected from, but not limited to, furyl, tetrahydrofuranyl, pyranyl, pyronyl, dioxinyl, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, azepinyl, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, diazepinyl, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkylcarbonyl, alkylcarboxy, alkylamino, and arylthio, which groups can be optionally substituted. Desirably, a substituted heterocyclic group has 1 to 4 substituents.

The term "arylthio" as used herein refers to the S(aryl) group, where the point of attachment is through the sulfur-atom and the aryl group can be optionally substituted.

The term "alkoxy" as used herein refers to the O(alkyl) group, where the point of attachment is through the oxygen-atom and the alkyl group is optionally substituted.

The term "thioalkoxy" as used herein refers to the S(alkyl) group, where the point of attachment is through the sulfur-atom and the alkyl group is optionally substituted.

The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "alkylamino" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The compounds described herein encompass tautomeric forms of the structures provided herein characterized by the bioactivity of the drawn structures. Further, the compounds described herein can be used in the form of salts derived from pharmaceutically or physiologically acceptable acids, bases, alkali metals and alkaline earth metals.

Pharmaceutically acceptable salts can be formed from organic and inorganic acids including, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, for example, sodium, lithium, or potassium, and organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-iso-propylpyrrolidinium, 1,4-dimethylpiperazinium, 1-n-butyl piperidinium, 2-methyl-piperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds described herein can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

As described herein, the compounds described herein and/or salts, prodrugs or tautomers thereof, are delivered in regimens therapeutic or prophylactic purposes, as described herein.

The compounds discussed herein also encompass "metabolites" which are unique products formed by processing the compounds described herein by the cell or subject. Desirably, metabolites are formed in vivo.

The compounds described herein are readily prepared by one of skill in the art according to the following schemes from commercially available starting materials or starting materials which can be prepared using literature procedures. These schemes show the preparation of representative compounds. Variations on these methods, or other methods known in the art, can be readily performed by one of skill in the art given the information provided herein.

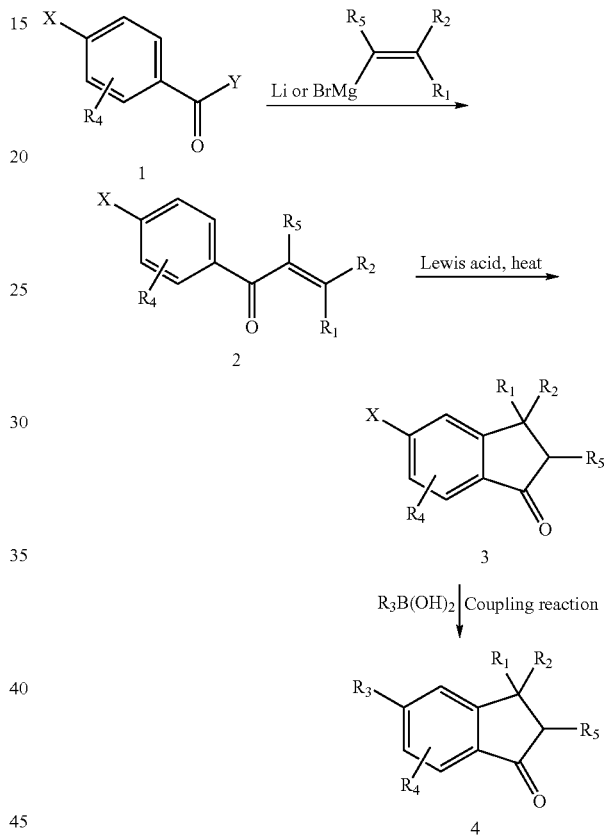

As illustrated in Scheme I, access to ketones 2 can be achieved by reaction of an appropriately substituted benzoic acid or its derivatives such as Weinreb amides 1 with a suitable organo lithium or Grignard reagent. The reaction can be executed in an aprotic solvent including but not limited to THF or diethyl ether at a suitable temperature ranging from −78° C. to room temperature under a blanket of inert atmosphere such as nitrogen or argon. To prevent the formation of carbinol side products, a reversing quenching procedure (pouring the reaction mixture to a diluted aqueous acidic solution such as hydrogen chloride solution) is preferred. An alternative way to work up the reaction included but not limited to an addition of trialkylsilyl chloride or equivalent to the reaction before quenching the reaction mixture with a diluted aqueous acidic solution. Cyclization of ketones 2 to afford indanones 3 can be effected with a suitable Lewis acid such as polyphosphoric acid (PPA) and aluminum chloride in an aprotic solvent such as chlorobenzene, xylene, the Dowtherm® A reagent, and nitrobenzene at the temperature ranging from room temperature to refluxing temperature of the solvent used. Formation of 5-aryl indanones 4, compounds described herein, can be achieved by a number of coupling reactions including Suzuki and Stille protocols. These reactions are commonly performed in the presence of a transition metallic catalyst, e.g., palladium or nickel complex often with phosphino ligands, e.g., triphenylphosphine ($Ph_3P$), 1,1'-bis(diphenylphosphino)ferrocene (dppf), or 1,2-bis(diphenylphosphino)ethane (dppe). Under this catalytic condition, an appropriately substituted aryl nucleophilic reagent, e.g., aryl boronic acid, arylstannane, or aryl zinc compound, can be coupled with 3 to produce the compounds described herein, 5-aryl indanones 4. The commonly used bases in the reaction include but not limited to sodium bicarbonate, sodium carbonate, potassium phosphate, barium carbonate, cesium fluoride, and potassium acetate. The most commonly used solvents in these reactions include benzene, toluene, dimethylformamide (DMF), isopropanol, ethanol, dimethoxyethane (DME), and ether. The coupling reaction is generally executed under an inert atmosphere such as nitrogen or argon at temperatures ranging from room temperature to 95° C. In the case when an appropriate aryl nucleophilic reagent is not available, the 5-halogen of 3 can be converted to the borate or stannane, which can be coupled with an appropriate aryl halide such as aryl bromide or aryl iodide using any coupling reaction described above to yield compounds 4.

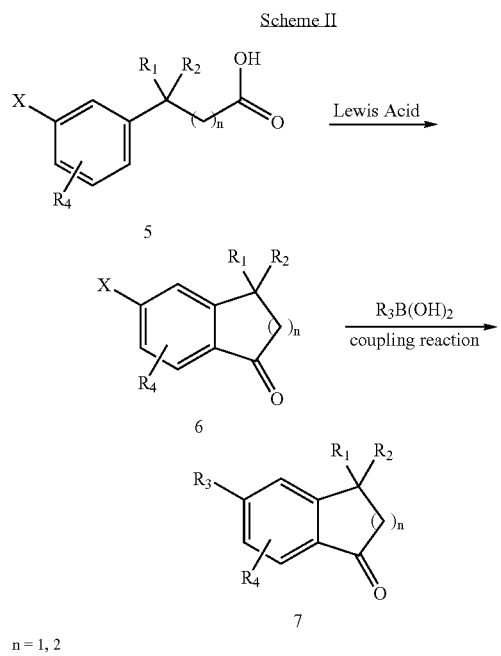

n = 1, 2

Alternatively, indanones as well as their six-member ring analogs, 3,4-dihydro-2H-naphthalen-1-ones 6, can be furnished from appropriately substituted 3-phenyl-propionic acids or 4-phenyl-butyric acids 5 as depicted in scheme II. Preferably, acids 5 are activated by converted into their corresponding carbonyl chloride or anhydrides by reacting with a suitable agent such as thionyl chloride or oxalyl chloride. The activated intermediates can be then in situ cyclized to form 6 using a Friedel-Crafts acylation protocol by addition of an appropriate Lewis acid such aluminum chloride or tin chloride in a suitable solvent such as benzene, chlorobenzene, and nitrobenzene at the temperature ranging from room temperature to refluxing temperature of the solvent used. Formation of 5-aryl indanones or 6-aryl 3,4-dihydro-2H-naphthalen-1-ones 7, the compounds described herein, can be readily effected using typical aforementioned coupling procedures as illustrated in Scheme I.

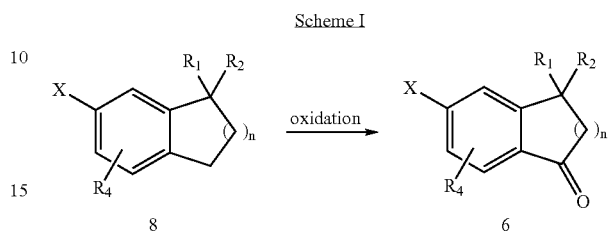

Indanones or 3,4-dihydro-2H-naphthalen-1-ones 6 can also be prepared via oxidation of appropriately substituted indans or 1,2,3,4-tetrahydro-naphthalenes using a suitable oxidant such as chromium (VI) oxide or manganese (IV) oxide in a suitable solvent such as water and acetic acid as depicted in scheme III. Conversion of 6 to 7 can be readily effected via the aforementioned coupling protocols.

Acyclic 1-(4-substituted-phenyl)-alkanones 10 can be furnished from reaction of an appropriately substituted benzoic acid or its suitable derivative such as Weinreb amide 9 with a suitable organo lithium or Grignard reagent as illustrated in scheme IV and this transformation can be executed aforementioned for the preparation of ketones 2 in scheme I. Followed the same coupling procedures as described above, the compounds described herein 11, can be furnished by reacting ketones 10 with an appropriate aryl nucleophilic reagent such as aryl boronic acid.

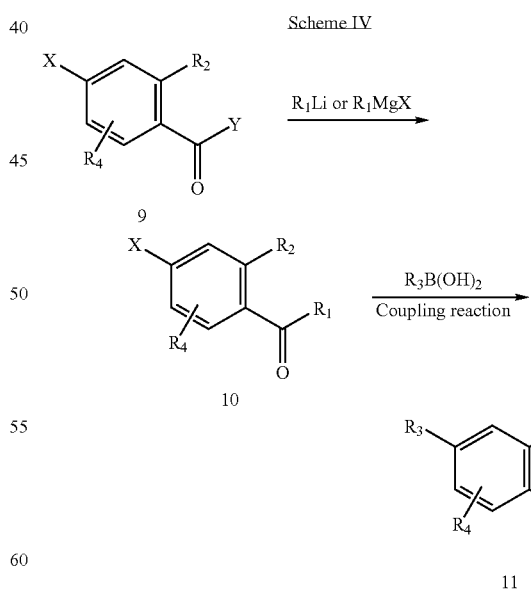

Also provided are pharmaceutical compositions containing one or more compounds described herein and a pharmaceutically acceptable carrier or excipient. Also provided are methods of treatment which include administering to a mammal a pharmaceutically effective amount of one or more compounds as described as progesterone receptor modulators.

The compounds described herein may be combined with one or more pharmaceutically acceptable carriers or excipients, for example, solvents, diluents and the like. Suitably, the compounds described herein are formulated for delivery to a subject by any suitable route including, e.g., transdermal, mucosal (intranasal, buccal, vaginal), oral, parenteral, among others. A variety of suitable delivery devices can be utilized and include, without limitation, tablets, caplets, capsules, gel tabs, dispersible powders, granules, suspensions, injectable solutions, transdermal patches, topical creams or gels, and vaginal rings, among others.

One particularly desirable pharmaceutical composition, from the standpoint of ease of preparation and administration, are solid compositions, particularly tablets and hard-filled or liquid-filled capsules. Oral administration of the compounds is most desirable.

The compounds described herein may be administered orally as well as by intravenous, intramuscular, or subcutaneous routes. Solid carriers include starch, lactose, dicalcium phosphate, microcrystalline cellulose, sucrose and kaolin. Liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, butylatedhydroxytoluene (BHT) and butylatedhydroxyanisole (BHA).

When formulated for oral delivery, the compounds described herein can be in the form of a tablet, capsule, caplet, gel tab, dispersible powders, granules, or suspensions. In one embodiment, the compound can be combined with suspending agents, including about 0.05 to about 5% of suspending agent, syrups containing, for example, about 10 to about 50% of sugar, and/or elixirs containing, for example, about 20 to about 50% ethanol, and the like.

The compounds described herein may also be administered parenterally or intraperitoneally. Solutions or suspensions of the compounds described herein as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. In one embodiment, the solutions or suspensions containing the compounds described herein can contain about 0.05 to about 5% suspending agent in an isotonic medium. Such pharmaceutical preparations may contain, for example, about 25 to about 90% of the compound in combination with the carrier. Desirably, the pharmaceutical preparation contains about 5% and 60% by weight of the compound.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds described herein may also be administered via a vaginal ring. Suitably, use of the vaginal ring is timed to cycle to which the compound is being administered, including a 28-day cycle. However, the vaginal ring can be inserted for longer or shorter periods of time. See, U.S. Pat. Nos. 5,972,372; 6,126,958; and 6,125,850, which are hereby incorporated by reference, for formulations of the vaginal ring that can be used.

The compound can also be delivered via a transdermal patch. Suitably, use of the patch is timed to the length of the cycle, including a 28 day cycle. However, the patch can remain in place for longer or shorter periods of time.

These compounds can be utilized in methods of contraception, hormone replacement therapy, the treatment and/or prevention of benign and malignant neoplastic disease including including uterine myometrial fibroids, endometriosis, benign prostatic hypertrophy, carcinomas and adenocarcinomas of the endometrium, ovary, breast, colon, prostate, pituitary, meningioma and other hormone-dependent tumors, and the treatment of cycle-related symptoms, dysmenorrheal, dysfunctional uterine bleeding, symptoms of premenstrual syndrome and premenstrual dysphoric disorder, and for inducing amenorrhea. Additional uses of the present progesterone receptor modulators include the synchronization of estrus in livestock. In one embodiment, the neoplastic disease is hormone-dependent.

The term "cycle-related symptoms" as used herein refers to psychological and physical symptoms associated with a woman's menstrual cycle arising in the luteal phase of the menstrual cycle. It has been reported that most women report experiencing cycle-related symptoms. The symptoms generally disappear after the onset of menstruation, and the patient is free from symptoms during the rest of the follicular phase. The cyclical nature of the symptom variations is characteristic of cycle-related symptoms.

Cycle-related symptoms occur in about 95% of women who experience some physical or mood changes with their menstrual cycles. Only about one-third of those women experiences moderate to severe cycle-related symptoms. Women vary in the number, type, severity, and pattern of symptoms before menstruation. One thing common to all the types of cyclic-related symptoms is the decrease or elimination of the symptoms in the two weeks after menstruation up to ovulation.

The term "cycle-related symptoms" refers to psychological symptoms (for example, mood change, irritability, anxiety, lack of concentration, or decrease in sexual desire) and physical symptoms (for example, dysmenorrhea, breast tenderness, bloating, fatigue, or food cravings) associated with a woman's menstrual cycle. Cycle-related symptoms occur after ovulation but before menses and usually terminate at the start of the menstrual period or shortly thereafter. Cycle-related symptoms include, but are not limited to, dysmenorrhea and moderate to severe cycle-related symptoms.

When utilized for these purposes, the compounds of formulas I, II, or III can be administered in combination with other agents, as well as in combination with each other. Such agents include, without limitation, progestins, anti-progestins, estrogens, among others. Progestins can include, without limitation, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, (17-deacetyl)norgestimate. Estrogens can include, without limitation, ethinyl estradiol.

In one embodiment, a patient or subject being treated is a mammalian subject and typically a female. Desirably, the subject is a human. However, as used herein, a female can include non-human mammals, e.g., cattle or livestock, horses, pigs, domestic animals, etc.

Methods of inducing contraception, providing hormone replacement therapy, or treating cycle-related symptoms are provided, including administering to a mammal in need thereof a pharmaceutically effective amount of a compound described herein. In one embodiment, the compound of formula I utilized in the method is of formula I, formula II, or formula III.

In another embodiment, methods of inducing contraception, providing hormone replacement therapy, or treating cycle-related symptoms are provided, including administering to a mammal in need thereof a pharmaceutically effective amount of a compound of formula I:

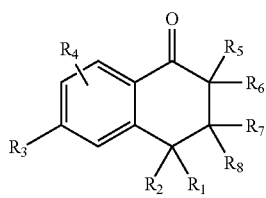

I wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted aryl; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C$-$COR^D$; or (iii) a 5 or 6 membered heteroaryl ring containing in its backbone 1 or 3 $NR^C$ heteroatoms and substituted with 0 to 3 substituents selected among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl; or a pharmaceutically acceptable salt thereof.

In another embodiment, a method of treating or preventing benign or malignant neoplastic disease is provided, including administering to a mammal in need thereof a pharmaceutically effective amount of a compound of formula I:

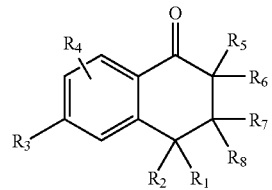

I wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) a benzene ring of the structure:

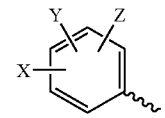

wherein, X is selected from among halogen, CN, $C_1$ to $C_4$ alkyl, substituted $C_1$ to $C_4$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_4$ alkoxy, substituted $C_1$ to $C_4$ alkoxy, $C_1$ to $C_4$ thioalkoxy, substituted $C_1$ to $C_4$ thioalkoxy, amino, $C_1$ to $C_4$ alkylamino, substituted $C_1$ to $C_4$ alkylamino, $NO_2$, $C_1$ to $C_3$ perfluoroalkyl, 5 or 6 membered heteroaryl ring containing in its backbone 1 to 3 heteroatoms, $COR^C$, $OCOR^C$, or $NR^DCOR^C$; Y and Z are independent substituents selected from among H, halogen, CN, $NO_2$, $C_1$ to $C_4$ alkoxy, $C_1$ to $C_4$ alkyl, and $C_1$ to $C_4$ thioalkoxy; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; or (iii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl; or a pharmaceutically acceptable salt thereof.

Also provided is a method of inducing contraception, providing hormone replacement therapy, treating cycle-related symptoms, or treating or preventing benign or malignant neoplastic disease, including administering to a mammal in need thereof a pharmaceutically effective amount of a compound of formula II:

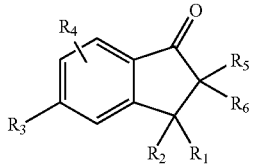

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted benzene ring; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C COR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C-COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$ and $R_6$ are, independently, H, F, or $C_1$ to $C_3$ alkyl; or a pharmaceutically acceptable salt thereof.

In one embodiment, when utilized in the method, the compound is 1-methyl-5-(3-methyl-1-oxo-2,3-dihydro-1H-inden-5-yl)-1H-pyrrole-2-carbonitrile; 5-(3,3-dimethyl-1-oxo-2,3-dihydro-1H-inden-5-yl)-1-methyl-1H-pyrrole-2-carbonitrile; 1-methyl-5-(1-oxo-2,3-dihydro-1H-inden-5-yl)-1H-pyrrole-2-carbonitrile; 4-acetyl-1-methyl-5-(1-oxo-2,3-dihydro-1H-inden-5-yl)-1H-pyrrole-2-carbonitrile; 5-(5-chlorothien-2-yl)-3,3-dimethylindan-1-one; 3,3-dimethyl-5-thien-3-yl-indan-1-one; 5-(3-acetylphenyl)indan-1-one; 5-(4-chlorophenyl)-3,3-dimethylindan-1-one; 4-(1-oxo-2,3-dihydro-1H-inden-5-yl)benzonitrile; 3-(1-oxo-2,3-dihydro-1H-inden-5-yl)benzonitrile; 3,3-dimethyl-5-(4-methylphenyl)indan-1-one; 5-(4-methoxyphenyl)-3,3-dimethylindan-1-one; 5-(3-chlorophenyl)-3,3-dimethylindan-1-one; 3,3-dimethyl-5-(3-methylphenyl)indan-1-one; 5-(3-methoxyphenyl)-3,3-dimethylindan-1-one; 5-(3,5-dichlorophenyl)-3,3-dimethylindan-1-one; 5-(2-chlorophenyl)-3,3-dimethylindan-1-one; 5-(3,4-dichlorophenyl)-3,3-dimethylindan-1-one; 5-(2,3-dichlorophenyl)-3,3-dimethylindan-1-one; 5-(2,5-dichlorophenyl)-3,3-dimethylindan-1-one; 5-(2,4-dichlorophenyl)-3,3-dimethylindan-1-one; 3,3-dimethyl-5-phenylindan-1-one; 5-(3-chloro-4-fluorophenyl)-3,3-dimethylindan-1-one; 3,3-dimethyl-5-[3-(trifluoromethyl)phenyl]indan-1-one; 3,3-dimethyl-5-[4-(trifluoromethyl)phenyl]indan-1-one; 5-[4-(dimethylamino)phenyl]-3,3-dimethylindan-1-one; 5-[3-(dimethylamino)phenyl]-3,3-dimethylindan-1-one; 5-(3,4-difluorophenyl)-3,3-dimethylindan-1-one; 5-[3-(ethylsulfonyl)phenyl]-3,3-dimethylindan-1-one; 3-(3,3-dimethyl-1-oxo-2,3-dihydro-1H-inden-5-yl)-5-fluorobenzonitrile; 5-(4-acetylphenyl)-3,3-dimethylindan-1-one; 5-(3-acetylphenyl)-3,3-dimethylindan-1-one; 5-(2-acetylphenyl)-3,3-dimethylindan-1-one; 4-(3,3-dimethyl-1-oxo-2,3-dihydro-1H-inden-5-yl)benzonitrile; 3-(3,3-dimethyl-1-oxo-2,3-dihydro-1H-inden-5-yl)benzonitrile; and 2-(3,3-dimethyl-1-oxo-2,3-dihydro-1H-inden-5-yl)benzonitrile.

Also provided is a method of providing hormone replacement therapy or treating cycle-related symptoms, including administering to a mammal in need thereof a pharmaceutically effective amount of a compound of formula III:

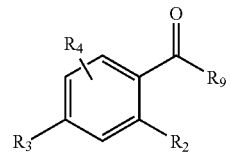

wherein, $R_2$ is selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_3$ is aryl, substituted aryl, heteroaryl, or substituted heteroaryl; $R_4$ is H, halogen, CN, OH, $NO_2$, alkoxy, or lower alkyl; $R_9$ is H, F, or $C_1$ to $C_3$ alkyl; or a pharmaceutically acceptable salt thereof.

Methods of inducing contraception or treating or preventing benign or malignant neoplastic disease, are also provided and include administering to a mammal in need thereof a pharmaceutically effective amount of a compound of formula III:

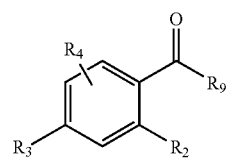

wherein, $R_2$ is selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_3$ is heteroaryl or substituted heteroaryl; $R_4$ is H, halogen, CN, OH, $NO_2$, alkoxy, or lower alkyl; $R_9$ is H, F, or $C_1$ to $C_3$ alkyl; or a pharmaceutically acceptable salt thereof.

In one embodiment, when utilized in the methods described herein, the compound of formula III is selected from among 5-(4-acetylphenyl)-1-methyl-1H-pyrrole-2-carbonitrile; 1-methyl-5-(4-propionylphenyl)-1H-pyrrole-2-carbonitrile; 1-methyl-5-[4-(thien-2-yl-carbonyl)phenyl]-1H-pyrrole-2-carbonitrile; 5-(4-benzoylphenyl)-1-methyl-1H-pyrrole-2-carbonitrile; and 5-[4-(2,2-dimethylpropanoyl)phenyl]-1-methyl-1H-pyrrole-2-carbonitrile.

In another embodiment, when utilized in the methods described herein, the compounds include those wherein $R_1$ and $R_2$ are, independently, H or $C_1$ to $C_6$ alkyl; $R_3$ is a 5 membered heteroaryl ring containing in its backbone 1 $NR^C$ heteroatom and substituted with 0 to 3 substituents selected from among H, CN, or $C_1$ to $C_3$ alkyl; $R_4$, $R_5$, $R_6$, $R_7$, and $R_8$ are H.

In a further embodiment, when utilized in the methods described herein, the compounds include those wherein $R_3$ is 1-methyl-2-cyanopyrrole, 1-methyl-2-cyano-4-acetylpyrrole or 2-chlorothiophene.

In yet another embodiment, when utilized in the methods described herein, the compounds include those wherein $R_1$ is heteroaryl or aryl.

In still a further embodiment, when utilized in the methods described herein, the compounds include those wherein $R_3$ is 4-cyanophenyl, 3-cyanophenyl, 3-acetylphenyl, 3-chlorophenyl, 3-chloro-4-fluorophenyl, 3-trifluoromethylphenyl, 3-fluorophenyl, 3,4-difluorophenyl, 3-methoxyphenyl, 3-methylphenyl, 4-chlorophenyl, 4-methylphenyl, 4-methoxyphenyl, 3,5-dichlorophenyl, 2-chlorophenyl, 3,4-dichlorophenyl, 2,3-dichlorophenyl, 2,5-dichlorophenyl, 2,4-dichlorophenyl, phenyl, 4-trifluoromethylphenyl, 4-diaminophenyl, 3-diaminophenyl, 3-ethylsulfonylphenyl, 3-fluoro-5-cyanophenyl, 4-acetylphenyl, 2-acetylphenyl, or 2-cyanophenyl.

In another embodiment, when utilized in the methods described herein, the compounds include those wherein $R_3$ is of the structure:

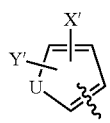

wherein, U is O, S, or $NR^C$; $R^6$ is H, $C_1$ to $C_3$ alkyl, or $COR^D$; $R^D$ is $C_1$ to $C_4$ alkyl; X' is selected from among halogen, CN, $NO_2$, $C_1$ to $C_3$ alkyl, and $C_1$ to $C_3$ alkoxy; and Y' is selected from among H and $C_1$ to $C_4$ alkyl.

In still another embodiment, when utilized in the methods described herein, the compounds include those wherein $R_3$ is of the structure:

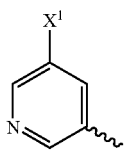

$X^1$ is halogen, CN, $C_1$ to $C_3$ alkoxy, or $NO_2$.

In yet a further embodiment, when utilized in the methods described herein, the compounds include those wherein $R_3$ is a benzene ring containing 0 to 3 substituents selected from among halogen, CN, $C_1$ to $C_4$ alkyl, substituted $C_1$ to $C_4$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ alkylamino, substituted $C_1$ to $C_3$ alkylamino, $NO_2$, $C_1$ to $C_3$ perfluoroalkyl, 5 or 6 membered heteroaryl ring containing in its backbone 1 to 3 heteroatoms, $COR^C$, $OCOR^C$, and $NR^DCOR^C$;

In another embodiment, when utilized in the methods described herein, the compounds include those wherein $R_3$ is a benzene ring of the structure:

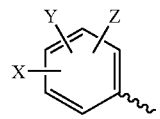

wherein, X is selected from among halogen, CN, $C_1$ to $C_4$ alkyl, substituted $C_1$ to $C_4$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_4$ alkoxy, substituted $C_1$ to $C_4$ alkoxy, $C_1$ to $C_4$ thioalkoxy, substituted $C_1$ to $C_4$ thioalkoxy, amino, $C_1$ to $C_4$ alkylamino, substituted $C_1$ to $C_4$ alkylamino, $NO_2$, $C_1$ to $C_3$ perfluoroalkyl, 5 or 6 membered heteroaryl ring containing in its backbone 1 to 3 heteroatoms, $COR^C$, $OCOR^C$, or $NR^DCOR^C$; Y and Z are independent substituents selected from among H, halogen, CN, $NO_2$, $C_1$ to $C_4$ alkoxy, $C_1$ to $C_4$ alkyl, and $C_1$ to $C_4$ thioalkoxy.

In yet a further embodiment, when utilized in the methods described herein, the compounds include those wherein $R_3$ is of the structure:

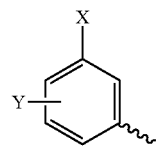

X is selected from among halogen, CN, $C_1$ to $C_3$ alkoxy, $C_1$ to $C_3$ alkyl, $NO_2$, $C_1$ to $C_3$ perfluoroalkyl, 5 membered heteroaryl ring containing in its backbone 1 to 3 heteroatoms, and $C_1$ to $C_3$ thioalkoxy; Y is selected from among H, halogen, CN, $NO_2$, $C_1$ to $C_3$ alkoxy, $C_1$ to $C_4$ alkyl, and $C_1$ to $C_3$ thioalkoxy.

The effective dosage of a compound described herein may vary depending on the particular compound employed, the mode of administration and the severity of the condition being treated. However, in general, satisfactory results are obtained when the compounds are administered at a daily dosage of about 0.5 to about 500 mg/kg of animal body weight, about 1 to about 400 mg/kg, about 5 to about 300 mg/kg, about 10 to about 250 mg/kg, about 50 to about 200 mg/kg, or about 100 to 150 mg/kg. For most large mammals, the total daily dosage is from about 1 to 100 mg. In one embodiment, the total daily dosage is from about 2 to 80 mg. This dosage regimen may be adjusted to provide the optimal therapeutic response. For example, several divided doses may be administered daily or the dose may be proportionally reduced as indicated by the exigencies of the therapeutic situation.

As previously noted, the compounds described herein may be administered via a vaginal ring. Suitably, use of the vaginal ring is timed to the 28 day cycle. In one embodiment, the ring is inserted into the vagina, and it remains in place for 3 weeks. During the fourth week, the vaginal ring is removed and menses occurs. The following week a new ring is inserted to be worn another 3 weeks until it is time for the next period. In another embodiment, the vaginal ring is inserted weekly, and is replaced for 3 consecutive weeks. Then, following 1 week without the ring, a new ring is inserted to begin a new regimen. In yet another embodiment, the vaginal ring is inserted for longer or shorter periods of time.

Further, the previously mentioned patch is applied via a suitable adhesive on the skin, where it remains in place for 1 week and is replaced weekly for a total period of 3 weeks. During the fourth week, no patch is applied and menses occurs. The following week a new patch is applied to be worn to begin a new regimen. In yet another embodiment, the patch remains in place for longer, or shorter periods of time.

When used for contraception, the method typically includes delivering a daily dosage unit containing a compound described herein for 28 consecutive days to a female of child-bearing age. Desirably, the method includes delivering the compound over a period of 21 to 27 consecutive days followed by 1 to 7 consecutive days in which no effective amount or no amount of the compound is delivered. Optionally, the period of 1 to 7 days in which no effective amount of the compound is delivered to the subject can involve delivery of a second phase of daily dosage units of 1 to 7 days of a pharmaceutically acceptable placebo. Alternatively, during this "placebo period", no placebo is administered.

In another embodiment, the method includes delivering a compound described herein for 21 consecutive days followed by 7 days in which no effective amount of the compound is delivered. Optionally, during these 7 days, a second phase of 7 daily dosage units of an orally and pharmaceutically acceptable placebo can be delivered. The compound may optionally be administered in combination with a progestin, antiprogestin, estrogen, or combination thereof.

In a further embodiment, the method includes delivering a compound described herein for 23 consecutive days followed by 5 days in which no effective amount of the compound is delivered. Optionally, during these 5 days, a second phase of 5 daily dosage units of an orally and pharmaceutically acceptable placebo can be delivered. The compound may optionally be administered in combination with a progestin, antiprogestin, estrogen, or combination thereof.

In yet another embodiment, the method includes delivering a compound described herein for 25 consecutive days followed by 3 days in which no effective amount of the compound is delivered. Optionally, during these 3 days, a second phase of 3 daily dosage units of an orally and pharmaceutically acceptable placebo can be delivered. The compound described herein may optionally be administered in combination with a progestin, antiprogestin, estrogen, or combination thereof.

In still a further embodiment, the method includes delivering a compound described herein for 27 consecutive days followed by 1 day in which no effective amount of the compound is delivered. Optionally, a second phase of 1 daily dosage unit of an orally and pharmaceutically acceptable placebo can be delivered. The compound may optionally be administered in combination with a progestin, antiprogestin, estrogen, or combination thereof.

In another embodiment, a method of contraception includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound of formula I, formula II, formula III, or combination thereof; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet a further embodiment, a method of contraception includes administering to a female of child bearing age for 28 consecutive days: (a) a first phase of from 14 to 24 daily dosage units of a compound of formula I, formula II, formula III, or combination thereof; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet another embodiment, a method of contraception is provided which includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound of (i), (ii), or (iii): (i) a compound of formula I:

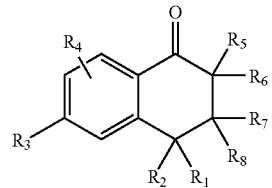

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; provided that both $R_1$ and $R_2$ are not H; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i) or (ii): (i) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl;

(ii) A Compound of Formula II:

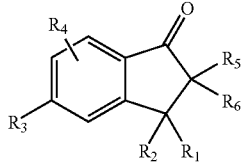

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted benzene ring; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$ and $R_6$ are, independently, H, F, or $C_1$ to $C_3$ alkyl; or (iii) a compound of formula III:

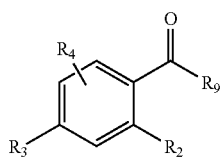

wherein, $R_2$ is selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_3$ is heteroaryl or substituted heteroaryl; $R_4$ is H, halogen, CN, OH, $NO_2$, alkoxy, or lower alkyl; $R_9$ is H, F, or $C_1$ to $C_3$ alkyl; a pharmaceutically acceptable salt thereof; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In a further embodiment, a method of contraception is provided which includes administering to a female of child bearing age for 28 consecutive days: (a) a first phase of from 14 to 24 daily dosage units of a compound of formula (i), (ii), or (iii): (i) a compound of formula I:

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; provided that both $R_1$ and $R_2$ are not H; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i) or (ii): (i) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl; or (ii) a compound of formula II:

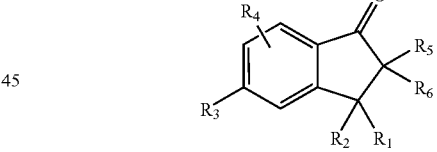

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted benzene ring; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, COR$^D$, and NR$^C$COR$^D$; or (ii) a 5 or 6 membered heteroaryl ring containing in its backbone 1 or 3 NR$^C$ heteroatoms and substituted with 0 to 3 substituents selected from among H, halogen, CN, NO$_2$, OH, amino, C$_1$ to C$_4$ alkyl, C$_1$ to C$_4$ alkoxy, C$_1$ to C$_4$ alkylamino, C=NOR$^C$, COR$^D$, and NR$^C$COR$^D$; R$^C$ is absent, H, C$_1$ to C$_4$ alkyl, substituted C$_1$ to C$_4$ alkyl, CN, or COR$^D$; R$^D$ is H, C$_1$ to C$_4$ alkyl, C$_1$ to C$_4$ alkoxy, or C$_1$ to C$_4$ alkylamino; R$_4$ is H, halogen, CN, OH, NO$_2$, alkoxy, or lower alkyl; R$_5$ and R$_6$ are, independently, H, F, or C$_1$ to C$_3$ alkyl; or (iii) a compound of formula III:

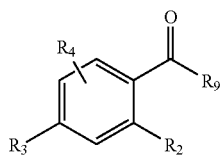

wherein, R$_2$ is selected from among H, halogen, C$_1$ to C$_6$ alkyl, CF$_3$, CF$_2$CF$_3$, C$_2$ to C$_6$ alkenyl, C$_2$ to C$_6$ alkynyl, C$_3$ to C$_8$ cycloalkyl, aryl, substituted aryl, heteroaryl, and substituted heteroaryl; R$_3$ is heteroaryl or substituted heteroaryl; R$_4$ is H, halogen, CN, OH, NO$_2$, alkoxy, or lower alkyl; R$_9$ is H, F, or C$_1$ to C$_3$ alkyl; a pharmaceutically acceptable salt thereof; (b) a second phase of from 1 to 11 daily dosage units, at a daily dosage of from about 2 to 50 mg, of a progestational agent equal in progestational activity to about 35 to about 100 μg levonorgestrel; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

Also included are kits or packages of pharmaceutical formulations designed for use in the regimens described herein. Suitably, the kits contain one or more PR antagonist compounds as described herein.

Advantageously, for use in the kits, the compound described herein is formulated for the desired delivery vehicle and route. For example, the compound can be formulated for oral delivery, parenteral delivery, vaginal ring, transdermal delivery, or mucosal delivery, as discussed in detail above. The kit is preferably a pack (e.g. a blister pack) containing daily doses arranged in the order in which they are to be taken.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional phases, including any second and third phases. To help facilitate compliance with each regimen, it is also preferred that the kits contain the placebo described for the final days of the cycle. It is further preferred that each package or kit contain a pharmaceutically acceptable package having indicators for each day of the 28-day cycle, such as a labeled blister package, dial dispenser, or other packages known in the art.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

In one embodiment, the kit is designed for daily oral administration over a 28-day cycle, desirably for one oral administration per day, and organized so as to indicate a single oral formulation or combination of oral formulations to be taken on each day of the 28-day cycle. Desirably each kit will include oral tablets to be taken on each the days specified; desirably one oral tablet will contain each of the combined daily dosages indicated. For example, a kit can contain 21 to 27 daily dosage units of an effective amount of the compound described herein and, optionally, 1 to 7 daily dosage units of a placebo and other appropriate components including, e.g., instructions for use.

In another embodiment, the kit is designed for weekly or monthly administration via a vaginal ring over a 28-day cycle. Suitably, such a kit contains individual packaging for each of the vaginal rings, i.e. one to three, required for a monthly cycle and other appropriate components, including, e.g., instructions for use.

In a further embodiment, the kit is designed for weekly or monthly administration via a transdermal patch over a 28-day cycle. Suitably, such a kit contains individual packaging for each of the patches, i.e. one to three, required for a monthly cycle and other appropriate components including, e.g., instructions for use.

In still another embodiment, the kit is designed for parenteral delivery of a compound described herein. Such a kit is typically designed for delivery at home and may include needles, syringes, and other appropriate packaging and instructions for use.

In yet another embodiment, the kit contains a compound described herein in a gel or cream formulation. Optionally, the kit can include appropriate packaging such as a tube or other container, an applicator, and/or instructions for use.

In a further embodiment, the kit includes (a) a first phase of from 14 to 21 daily dosage units of a progestational agent equal in progestational activity to about 35 to about 150 μg levonorgestrel; (b) a second phase of from 1 to 11 daily dosage units of a compound of formula I or II, each daily dosage unit containing said compound at a daily dosage of from about 2 to 50 mg, wherein said compound is (i), (ii), or (iii): (i) a compound of formula I:

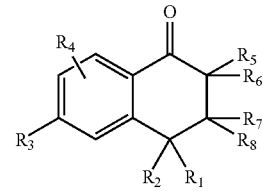

wherein, R$_1$ and R$_2$ are, independently, selected from among H, halogen, C$_1$ to C$_6$ alkyl, CF$_3$, CF$_2$CF$_3$, C$_2$ to C$_6$ alkenyl, C$_2$ to C$_6$ alkynyl, C$_3$ to C$_8$ cycloalkyl, aryl, substituted aryl, heteroaryl, and substituted heteroaryl; provided that both R$_1$ and R$_2$ are not H; or R$_1$ and R$_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, SO$_2$, and NR$^C$; wherein rings (a)-(c) are optionally substituted by 1 to 3 substituents selected from among F, Cl, and $C_1$ to $C_3$ alkyl; $R_3$ is (i) or (ii): (i) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl;

(ii) A Compound of Formula II:

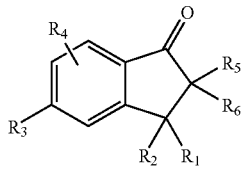

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted benzene ring; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$ and $R_6$ are, independently, H, F, or $C_1$ to $C_3$ alkyl; or (iii) a compound of formula III:

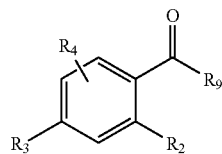

wherein, $R_2$ is selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_3$ is heteroaryl or substituted heteroaryl; $R_4$ is H, halogen, CN, OH, $NO_2$, alkoxy, or lower alkyl; $R_9$ is H, F, or $C_1$ to $C_3$ alkyl; or a pharmaceutically acceptable salt thereof; and a pharmaceutically acceptable salt thereof; and (c) a third phase of daily dosage units of an orally and pharmaceutically acceptable placebo; wherein the total number of the daily dosage units in the first phase, second phase and third phase equals 28.

In yet another embodiment, the kit includes (a) a first phase of from 14 to 21 daily dosage units of a compound of formula (i), (ii), or (iii): (i) a compound of formula I:

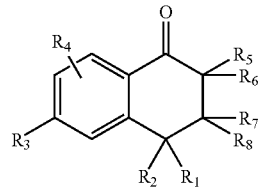

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; provided that both $R_1$ and $R_2$ are not H; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i) or (ii): (i) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$, $R_6$, $R_7$, and $R_8$ are, independently, H, F, or $C_1$ to $C_3$ alkyl;

(ii) A Compound of Formula II:

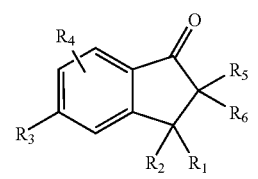

wherein, $R_1$ and $R_2$ are, independently, selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; or $R_1$ and $R_2$ are fused to form (a), (b), or (c): (a) a carbon-based 3 to 6 membered saturated spirocyclic ring; (b) a carbon-based 3 to 6 membered spirocyclic ring having in its backbone one or more carbon-carbon double bonds; or (c) a carbon-based 3 to 6 membered spirocyclic ring having in its backbone 1 to 3 heteroatoms selected from among O, S, SO, $SO_2$, and $NR^C$; wherein rings (a)-(c) are optionally substituted by 1 to 3 substituents selected from among F, Cl, and $C_1$ to $C_3$ alkyl; $R_3$ is (i), (ii), or (iii): (i) an optionally substituted benzene ring; (ii) a 5 or 6 membered heteroaryl ring containing in its backbone 1 to 3 heteroatoms selected from among O, S, SO, and $SO_2$ and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^CCOR^D$; or (ii) a 5 or 6 membered heteroaryl ring containing in its backbone 1 or 3 $NR^C$ heteroatoms and substituted with 0 to 3 substituents selected from among H, halogen, CN, $NO_2$, OH, amino, $C_1$ to $C_4$ alkyl, $C_1$ to $C_4$ alkoxy, $C_1$ to $C_4$ alkylamino, $C=NOR^C$, $COR^D$, and $NR^C$-$COR^D$; $R^C$ is absent, H, $C_1$ to $C_4$ alkyl, substituted $C_1$ to $C_4$ alkyl, CN, or $COR^D$; $R^D$ is H, $C_1$ to $C_4$ alkyl, $C_1$ to $C_4$ alkoxy, or $C_1$ to $C_4$ alkylamino; $R_4$ is H, halogen, CN, OH, $NO_2$, alkoxy, or lower alkyl; $R_5$ and $R_6$ are, independently, H, F, or $C_1$ to $C_3$ alkyl; or (iii) a compound of formula III:

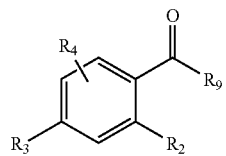

wherein, $R_2$ is selected from among H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, substituted aryl, heteroaryl, and substituted heteroaryl; $R_3$ is heteroaryl or substituted heteroaryl; $R_4$ is H, halogen, CN, OH, $NO_2$, alkoxy, or lower alkyl; $R_9$ is H, F, or $C_1$ to $C_3$ alkyl; or a pharmaceutically acceptable salt thereof; (b) a second phase of from 1 to 11 daily dosage units of a progestational agent equal in progestational activity to about 35 to about 150 μg levonorgestrel, each daily dosage unit containing said progestational agent at a daily dosage of from about 2 to 50 mg; and (c) a third phase of daily dosage units of an orally and pharmaceutically acceptable placebo; wherein the total number of the daily dosage units in the first phase, second phase and third phase equals 28.

The following examples are illustrative only and are not intended to be a limitation.

EXAMPLES

Example 1

5-(4-acetylphenyl)-1-methyl-1H-pyrrole-2-carbonitrile

To a stirred solution of 1-methyl-2-cyanopyrrole (1.6 g, 15 mmol) and triisopropyl borate (7.0 mL, 30 mmol) in tetrahydrofuran (THF—45 mL) at 0° C. was added lithium diisopropylamide (LDA—2.0 M in heptane/THF/ethylbenzene, 13.3 mL, 26.6 mmol) in a dropwise fashion over 45 minutes. The resulting solution was stirred at 0° C. for 1 hour. To the solution was added 1-(4-bromophenyl)-ethanone (1.0 g, 5 mmol) dissolved in glyme (45 mL), sodium carbonate (1.59 g, 15 mmol) dissolved in water (9 mL), and tetrakis(triphenylphosphine)palladium (0) (0.28 g, 0.25 mmol). The resulting solution was heated to reflux for 1.5 hours. The solution was cooled to room temperature and partitioned between a saturated aqueous ammonium chloride solution (50 mL) and ethyl acetate (80 mL). The organic layer was separated, dried over magnesium sulfate, filtered, and concentrated. The residue was purified on a silica gel column (20% ethyl acetate in hexane) and triturated with ether to give 5-(4-acetylphenyl)-1-methyl-1H-pyrrole-2-carbonitrile as a yellow solid (0.62 g, 55%). MS (ES) m/z 225.1; HRMS: calcd for $C_{14}H_{12}N_2O+H^+$, 225.1022; found (ESI, $[M+H]^+$), 225.1039.

Example 2

1-methyl-5-(3-methyl-1-oxo-2,3-dihydro-1H-inden-5-yl)-1H-pyrrole-2-carbonitrile

To a mixture of sodium chloride (1.23 g, 21.0 mmol) and aluminum chloride (5.0 g, 38.2 mmol) at 130° C. was added 1-(4-bromophenyl)-4-chlorobutan-1-one (1.0 g, 3.82 mmol) and the resulting mixture was heated to 180° C. for 20 minutes. The mixture was allowed to cool to room temperature and poured to a cold 1N aqueous HCl solution (300 mL). The mixture was extracted several times with dichloromethane. The combined organic layers were separated, dried over magnesium sulfate, filtered and concentrated to give 5-bromo-3-methyl-indan-1-one (0.77 g, 89%). The title compound, 1-methyl-5-(3-methyl-1-oxo-2,3-dihydro-1H-inden-5-yl)-1H-pyrrole-2-carbonitrile as an orange solid (0.65 g, 76%), was prepared from 5-bromo-3-methyl-indan-1-one and 1-methyl-2-cyanopyrrole according to the same coupling procedure as described in example 1. MS (ES) m/z 251.2; Anal. Calcd for $C_{16}H_{14}N_2O$: C, 76.78; H, 5.64; N, 11.19. Found: C, 76.49; H, 5.49; N, 11.10. HRMS: calcd for $C_{16}H_{14}N_2O+H^+$, 251.1179; found (ESI, $[M+H]^+$), 251.1179.

Example 3

5-(3,3-dimethyl-1-oxo-2,3-dihydro-1H-inden-5-yl)-1-methyl-1H-pyrrole-2-carbonitrile To a stirred solution of 1-(4-hydroxyphenyl)-3-methyl-but-2-en-1-one (1.0 g, 5.67 mmol) in dichlorobenzene (50 mL) was added aluminum chloride (1.97 g, 14.74 mmol). The mixture was heated to 150° C. for 4 hours. After cooled to room temperature, the reaction mixture was poured over ice and extracted with dichloromethane (3×80 mL). The organic layers were combined, dried over magnesium sulfate, filtered, and concentrated. The residue was purified on a silica gel column (20% ethyl acetate in hexane) to give 5-hydroxy-3,3-dimethylindan-1-one as a tan solid (0.32 g, 32%). MS m/z 177.

A solution of 5-hydroxy-3,3-dimethylindan-1-one in anhydrous pyridine at 0° C. was treated with triflic anhydride under an atmosphere of nitrogen. After completion of reaction indicated by thin layer chromatography, the reaction solution was poured onto a mixture of ice and 6N aqueous HCl solution and extracted with diethyl ether. The organic layers were combined, washed with saturated aqueous sodium bicarbonate solution, dried ($MgSO_4$), and concentrated to afford trifluoro-methanesulfonic acid 3,3-dimethyl-1-oxo-indan-5-yl ester that was used in the next step without further purification.

The title compound was prepared from trifluoro-methanesulfonic acid 3,3-dimethyl-1-oxo-indan-5-yl ester and 1-methyl-2-cyanopyrrole according to the same coupling procedure as described in example 1. MS (ES) m/z 265.1. HRMS: calcd for $C_{17}H_{16}N_2O+H^+$, 265.13354; found (ESI, [M+H]$^+$), 265.1332.

Example 4

1-methyl-5-(1-oxo-2,3-dihydro-1H-inden-5-yl)-1H-pyrrole-2-carbonitrile

The title compound was prepared from 5-bromo-1-indanone and 1-methyl-2-cyanopyrrole according to the coupling procedure as described in example 1. MS (ESI) m/z 237; HRMS: calcd for $C_{15}H_{12}N_2O+H^+$, 237.1022; found (ESI, [M+H]$^+$), 237.1003; Anal. Calcd for $C_{15}H_{12}N_2O$: C, 76.25; H, 5.12; N, 11.86. Found: C, 75.99; H, 4.92; N, 11.80.

Example 5

4-acetyl-1-methyl-5-(1-oxo-2,3-dihydro-1H-inden-5-yl)-1H-pyrrole-2-carbonitrile

To a stirred solution of 1-methyl-5-(1-oxo-2,3-dihydro-1H-inden-5-yl)-1H-pyrrole-2-carbonitrile (0.25 g, 1.0 mmol) in acetonitrile (25 mL) was added samarium iodide (0.5 g, 1.2 mmol) and acetyl chloride (1.75 mL, 24.6 mmol). The reaction mixture was heated in microwave to 120° C. for 10 minutes. The mixture was treated with a 10% aqueous HCl solution (50 mL) and extracted with ethyl acetate (3×50 mL). The organic layers were combined, dried over magnesium sulfate, filtered, and concentrated. The residue was purified on a silica gel column (30% ethyl acetate in hexane) to give 4-acetyl-1-methyl-5-(1-oxo-2,3-dihydro-1H-inden-5-yl)-1H-pyrrole-2-carbonitrile as a tan solid (0.025 g, 8%). MS (ESI) m/z 279; HRMS: calcd for $C_{17}H_{14}N_2O_2+H^+$, 279.1128; found (ESI, [M+H]$^+$), 279.1125.

Example 6

4-(1-oxo-2,3-dihydro-1H-inden-5-yl)benzonitrile

To a stirred solution of 5-bromo-1-indanone (0.40 g, 1.90 mmol) and 4-cyanophenyl boronic acid (0.36 g, 2.47 mmol) in glyme (17 mL) was added a solution of sodium carbonate (0.60 g, 5.70 mmol) in water (3 mL) and tetrakis(triphenylphosphine)palladium (0) (0.11 g, 0.10 mmol). The resulting solution was heated to reflux for 2.5 hours. The solution was cooled to room temperature and partitioned between a saturated aqueous ammonium chloride solution (50 mL) and ethyl acetate (80 mL). The organic layer was dried over magnesium sulfate, filtered, and concentrated. The residue was purified on a silica gel column (20% ethyl acetate in hexane) and triturated with ether to give 4-(1-oxo-2,3-dihydro-1H-inden-5-yl)benzonitrile as a white solid (0.35 g, 79%). MS (ESI) m/z 234.0936; HRMS: calcd for $C_{16}H_{11}NO+H^+$, 234.09134; found (ESI, [M+H]$^+$), 234.0936.

Example 7

3-(1-oxo-2,3-dihydro-1H-inden-5-yl)benzonitrile

The title compound was prepared from 5-bromo-1-indanone and 3-cyanophenyl boronic acid according to the coupling procedure as described in example 6. MS m/z 234; HRMS: calcd for $C_{16}H_{11}NO+H^+$, 234.09134; found (ESI, [M+H]$^+$), 234.0905;

Example 8

5-(3-acetylphenyl)indan-1-one

The title compound was prepared from 3-acetylphenyl boronic acid and 5-bromo-1-indanone according to the coupling procedure as described in example 6. MS (ESI) m/z 251; HRMS: calcd for $C_{17}H_{14}O_2+H^+$, 251.10666; found (ESI, [M+H]$^+$), 251.1077.

Example 9

1-methyl-5-(4-propionylphenyl)-1H-pyrrole-2-carbonitrile

The title compound was prepared from 1-(4-bromophenyl)-propan-1-one and 1-methyl-2-cyanopyrrole according to the coupling procedure as described in example 1. MS (ES) m/z 239.2; HRMS: calcd for $C_{15}H_{14}N_2O+H^+$, 239.1179; found (ESI, [M+H]$^+$), 239.1193.

Example 10

1-methyl-5-[4-(thien-2-ylcarbonyl)phenyl]-1H-pyrrole-2-carbonitrile

To a stirred solution of 4-bromobenzoyl chloride (20.0 g, 91.1 mmol) in dichloromethane (300 mL) at −78° C. was added triethylamine (28.0 mL, 200.0 mmol), and O,N-dimethylhydroxylamine hydrochloride (9.33 g, 95.6 mmol). The resulting solution was allowed to warm to room temperature, stirred for 1.5 hours, and then concentrated. The residue was triturated in acetone and the resulting solid was dissolved in ethyl acetate washed with water and brine. The organic layer was dried over magnesium sulfate, filtered, and concentrated to give 4-bromo-N-methoxy-N-methylbenzamide (18.6 g, 84%). To a solution of 4-bromo-N-methoxy-N-methylbenzamide (3.0 g, 12.29 mmol) in THF (30 mL) at 0° C. under nitrogen was added 2-thienyllithium (1.0 M in THF, 15 mL, 15 mmol) slowly over 10 minutes. The solution was stirred at 0° C. for 1 hour, poured into a saturated aqueous ammonium chloride solution (150 mL), and extracted several times with ethyl acetate. The combined organic layers were dried over magnesium sulfate, filtered, and concentrated. The residue was triturated with ether to give (4-bromophenyl)(thien-2-yl)methanone as a brown solid (1.1 g, 34%). MS (ES) m/z 266.9.

The title compound was prepared from (4-bromophenyl)(thien-2-yl)methanone and 1-methyl-2-cyanopyrrole according to the coupling procedure as described in example 1. MS (ES) m/z 293.1; HRMS: calcd for $C_{17}H_{12}N_2OS+H^+$, 293.0743; found (ESI, [M+H]$^+$), 293.0744.

Example 11

5-(4-benzoylphenyl)-1-methyl-1H-pyrrole-2-carbonitrile

The title compound was prepared from (4-bromophenyl)-phenyl-methanone and 1-methyl-2-cyanopyrrole according to the coupling procedure as described in example 1. MS (ES) m/z 287.1; HRMS: calcd for $C_{19}H_{14}N_2O+H^+$, 287.11789; found (ESI, [M+H]$^+$), 287.1185.

Example 12

6-(3-chlorophenyl)-3,4-dihydronaphthalen-1(2H)-one

Trifluoro-methanesulfonic acid 5-oxo-5,6,7,8-tetrahydro-naphthalen-2-yl ester was prepared from 6-hydroxy-3,4-dihydro-2H-naphthalen-1-one followed the triflation procedure as described in the example 3. MS (ESI) m/z 295.

The title compound was prepared from trifluoro-methanesulfonic acid 5-oxo-5,6,7,8-tetrahydro-naphthalen-2-yl ester and 3-chlorophenyl boronic acid according to the coupling procedure as described in example 6. MS (ES) m/z 257.1.

Example 13

1-methyl-5-(5-oxo-5,6,7,8-tetrahydronaphthalen-2-yl)-1H-pyrrole-2-carbonitrile The title compound was prepared from trifluoro-methanesulfonic acid 5-oxo-5,6,7,8-tetrahydro-naphthalen-2-yl ester and 1-methyl-2-cyanopyrrole according to the coupling procedure as described in example 1. MS (ES) m/z 251.2; HRMS: calcd for $C_{16}H_{14}N_2O+H^+$, 251.11789; found (ESI, [M+H]$^+$), 251.1186.

Example 14

6-(3-chloro-4-fluorophenyl)-3,4-dihydronaphthalen-1(2H)-one

The title compound was prepared from trifluoro-methanesulfonic acid 5-oxo-5,6,7,8-tetrahydro-naphthalen-2-yl ester and 3-chloro-4-fluorophenyl boronic acid according to the coupling procedure as described in example 6. MS (ESI) m/z 275.

Example 15

6-(4-chlorophenyl)-3,4-dihydronaphthalen-1(2H)-one

The title compound was prepared from trifluoro-methanesulfonic acid 5-oxo-5,6,7,8-tetrahydro-naphthalen-2-yl ester and 4-chlorophenyl boronic acid according to the coupling procedure as described in example 6. MS (ESI) m/z 257.

Example 16

6-[3-(trifluoromethyl)phenyl]-3,4-dihydronaphthalen-1(2H)-one

The title compound was prepared from trifluoro-methanesulfonic acid 5-oxo-5,6,7,8-tetrahydro-naphthalen-2-yl ester and 3-trifluoromethylhenyl boronic acid according to the coupling procedure as described in example 6. MS (ESI) m/z 291.

Example 17

6-(3-fluorophenyl)-3,4-dihydronaphthalen-1(2H)-one

The title compound was prepared from trifluoro-methanesulfonic acid 5-oxo-5,6,7,8-tetrahydro-naphthalen-2-yl ester and 3-fluorophenyl boronic acid according to the coupling procedure as described in example 6. MS (ESI) m/z 241.

Example 18

6-(3,4-difluorophenyl)-3,4-dihydronaphthalen-1(2H)-one

The title compound was prepared from trifluoro-methanesulfonic acid 5-oxo-5,6,7,8-tetrahydro-naphthalen-2-yl ester and 3,4-difluorophenyl boronic acid according to the coupling procedure as described in example 6. MS (ESI) m/z 259.

Example 19

6-(3-methoxyphenyl)-3,4-dihydronaphthalen-1(2H)-one

The title compound was prepared from trifluoro-methanesulfonic acid 5-oxo-5,6,7,8-tetrahydro-naphthalen-2-yl ester and 3-methoxyphenyl boronic acid according to the coupling procedure as described in example 6. MS (ESI) m/z 253.

Example 20

6-(3-methylphenyl)-3,4-dihydronaphthalen-1(2H)-one

The title compound was prepared from trifluoro-methanesulfonic acid 5-oxo-5,6,7,8-tetrahydro-naphthalen-2-yl ester and 3-methylphenyl boronic acid according to the coupling procedure as described in example 6. MS (ESI) m/z 237.

Example 21

5-(4-chlorophenyl)-3,3-dimethylindan-1-one

To a stirred solution of trifluoro-methanesulfonic acid 3,3-dimethyl-1-oxo-indan-5-yl ester (0.25 g, 0.81 mmol) in glyme (7 mL) was added 4-chlorophenyl boronic acid (0.19 g, 1.22 mmol), a solution of sodium carbonate (0.26 g, 2.43 mmol) in water (1.5 mL), and tetrakis(triphenylphosphine) palladium (0) (0.05 g, 0.04 mmol). The resulting solution was heated to reflux for 2 hours. The mixture was cooled to room temperature, concentrated, taken up in ethyl acetate and filtered through a pad of the Celite® reagent. The filtrate was concentrated and the residue was purified by Gilson high performance liquid chromatography (HPLC—10 to 100 acetonitrile in water) to afford 5-(4-chlorophenyl)-3,3-dimethylindan-1-one as a white solid. (0.11 g, 50%). MS (ES) m/z 271.0; HRMS: calcd for $C_{17}H_{15}ClO+H^+$, 271.0884; found (ESI, [M+H]$^+$), 271.0877.

Example 22

5-(3,5-dimethylisoxazol-4-yl)-3,3-dimethylindan-1-one

The title compound was prepared from trifluoro-methanesulfonic acid 3,3-dimethyl-1-oxo-indan-5-yl ester and 3,5-dimethylisoxazole-4-boronic acid according to the coupling procedure described in example 21. MS m/z 256; HRMS: calcd for $C_{16}H_{17}NO_2+H^+$, 256.13321; found (ESI, [M+H]$^+$), 256.1343.

Example 23

5-(5-chlorothien-2-yl)-3,3-dimethylindan-1-one

The title compound was prepared from trifluoro-methanesulfonic acid 3,3-dimethyl-1-oxo-indan-5-yl ester and 5-chlorothien-2-yl boronic acid according to the procedure described in example 21. MS m/z 277; HRMS: calcd for $C_{15}H_{13}ClOS+H^+$, 277.04484; found (ESI, $[M+H]^+$), 277.0444.

Example 24

3,3-dimethyl-5-thien-3-ylindan-1-one

The title compound was prepared from trifluoro-methanesulfonic acid 3,3-dimethyl-1-oxo-indan-5-yl ester and thien-3-yl boronic acid according to the procedure described in example 21. MS m/z 243; HRMS: calcd for $C_{15}H_{14}OS+H^+$, 243.08381; found (ESI, $[M+H]^+$), 243.084.

Example 25

5-[4-(2,2-dimethylpropanoyl)phenyl]-1-methyl-1H-pyrrole-2-carbonitrile

The title compound was prepared from 1-(4-bromophenyl)-2,2-dimethylpropan-1-one and 1-methyl-2-cyanopyrrole according to the coupling procedure described in example 1. MS m/z 267; HRMS: calcd for $C_{17}H_{18}N_2O+H^+$, 267.14919; found (ESI, $[M+H]^+$), 267.1494.

Example 26

3,3-dimethyl-5-(4-methylphenyl)indan-1-one

The title compound was prepared from trifluoro-methanesulfonic acid 3,3-dimethyl-1-oxo-indan-5-yl ester and 4-methylphenyl boronic acid according to the procedure described in example 21. MS (ES) m/z 251.1; HRMS: calcd for $C_{18}H_{18}O+H^+$, 251.14304; found (ESI, $[M+H]^+$), 251.1431.

Example 27

5-(4-methoxyphenyl)-3,3-dimethylindan-1-one

The title compound was prepared from trifluoro-methanesulfonic acid 3,3-dimethyl-1-oxo-indan-5-yl ester and 4-methoxyphenyl boronic acid according to the procedure described in example 21. MS (ES) m/z 267.1. HRMS: calcd for $C_{18}H_{18}O_2+H^+$, 267.13796; found (ESI, $[M+H]^+$), 267.1373.

Example 28

5-(3-chlorophenyl)-3,3-dimethylindan-1-one

The title compound was prepared from trifluoro-methanesulfonic acid 3,3-dimethyl-1-oxo-indan-5-yl ester and 3-chlorophenyl boronic acid according to the procedure described in example 21. MS (ES) m/z 271.1; HRMS: calcd for $C_{17}H_{15}ClO+H^+$, 271.08842; found (ESI, $[M+H]^+$), 271.0881.

Example 29

3,3-dimethyl-5-(3-methylphenyl)indan-1-one

The title compound was prepared from trifluoro-methanesulfonic acid 3,3-dimethyl-1-oxo-indan-5-yl ester and 3-methylphenyl boronic acid according to the procedure described in example 21. MS (ES) m/z 251.2; HRMS: calcd for $C_{18}H_{18}O+H^+$, 251.14304; found (ESI, $[M+H]^+$), 251.1428.

Example 30

5-(3-methoxyphenyl)-3,3-dimethylindan-1-one

The title compound was prepared from trifluoro-methanesulfonic acid 3,3-dimethyl-1-oxo-indan-5-yl ester and 3-methoxyphenyl boronic acid according to the procedure described in example 21. MS (ES) m/z 267.2; HRMS: calcd for $C_{18}H_{18}O_2+H^+$, 267.13796; found (ESI, $[M+H]^+$), 267.1386.

Example 31

5-(3,5-dichlorophenyl)-3,3-dimethylindan-1-one

The title compound was prepared from trifluoro-methanesulfonic acid 3,3-dimethyl-1-oxo-indan-5-yl ester and 3,5-dichlorophenyl boronic acid according to the procedure described in example 21. MS (ES) m/z 305.1; HRMS: calcd for $C_{17}H_{14}Cl_2O+H^+$, 305.04944; found (ESI, $[M+H]^+$), 305.0509.

Example 32

5-(2-chlorophenyl)-3,3-dimethylindan-1-one

The title compound was prepared from trifluoro-methanesulfonic acid 3,3-dimethyl-1-oxo-indan-5-yl ester and 2-chlorophenyl boronic acid according to the procedure described in example 21. MS (ES) m/z 271.1; HRMS: calcd for $C_{17}H_{15}ClO+H^+$, 271.08842; found (ESI, $[M+H]^+$), 271.088.

Example 33

5-(3,4-dichlorophenyl)-3,3-dimethylindan-1-one

The title compound was prepared from trifluoro-methanesulfonic acid 3,3-dimethyl-1-oxo-indan-5-yl ester and 3,4-dichlorophenyl boronic acid according to the procedure described in example 21. MS (ES) m/z 305.1; HRMS: calcd for $C_{17}H_{14}Cl_2O+H^+$, 305.04944; found (ESI, $[M+H]^+$), 305.0505.

Example 34

5-(2,3-dichlorophenyl)-3,3-dimethylindan-1-one

The title compound was prepared from trifluoro-methanesulfonic acid 3,3-dimethyl-1-oxo-indan-5-yl ester and 2,3-dichlorophenyl boronic acid according to the procedure described in example 21. MS (ES) m/z 305.1; HRMS: calcd for $C_{17}H_{14}Cl_2O+H^+$, 305.04944; found (ESI, $[M+H]^+$), 305.0504.

Example 35

5-(2,5-dichlorophenyl)-3,3-dimethylindan-1-one

The title compound was prepared from trifluoro-methanesulfonic acid 3,3-dimethyl-1-oxo-indan-5-yl ester and 2,5-dichlorophenyl boronic acid according to the procedure described in example 21. MS m/z 305; HRMS: calcd for $C_{17}H_{14}Cl_2O+H^+$, 305.04944; found (ESI, [M+H]$^+$), 305.0502.

Example 36

5-(2,4-dichlorophenyl)-3,3-dimethylindan-1-one

The title compound was prepared from trifluoro-methanesulfonic acid 3,3-dimethyl-1-oxo-indan-5-yl ester and 2,4-dichlorophenyl boronic acid according to the procedure described in example 21. MS m/z 305; HRMS: calcd for $C_{17}H_{14}Cl_2O+H^+$, 305.04944; found (ESI, [M+H]$^+$), 305.0494.

Example 37

3,3-dimethyl-5-phenylindan-1-one

The title compound was prepared from trifluoro-methanesulfonic acid 3,3-dimethyl-1-oxo-indan-5-yl ester and phenyl boronic acid according to the procedure described in example 21. MS m/z 237; HRMS: calcd for $C_{17}H_{16}O+H^+$, 237.12739; found (ESI, [M+H]$^+$), 237.1271.

Example 38

5-(3-chloro-4-fluorophenyl)-3,3-dimethylindan-1-one

The title compound was prepared from trifluoro-methanesulfonic acid 3,3-dimethyl-1-oxo-indan-5-yl ester and 3-chloro-4-fluorophenyl boronic acid according to the procedure described in example 21. MS m/z 289; HRMS: calcd for $C_{17}H_{14}ClFO+H^+$, 289.07900; found (ESI, [M+H]$^+$), 289.0785.

Example 39

3,3-dimethyl-5-[3-(trifluoromethyl)phenyl]indan-1-one

The title compound was prepared from trifluoro-methanesulfonic acid 3,3-dimethyl-1-oxo-indan-5-yl ester and 3-trifluoromethylphenyl boronic acid according to the procedure described in example 21. MS m/z 305; HRMS: calcd for $C_{18}H_{15}F_3O+H^+$, 305.11478; found (ESI, [M+H]$^+$), 305.1142.

Example 40

3,3-dimethyl-5-[4-(trifluoromethyl)phenyl]indan-1-one

The title compound was prepared from trifluoro-methanesulfonic acid 3,3-dimethyl-1-oxo-indan-5-yl ester and 4-(trifluoromethyl)phenyl boronic acid according to the procedure described in example 21. MS m/z 305; HRMS: calcd for $C_{18}H_{15}F_3O+H^+$, 305.11478; found (ESI, [M+H]$^+$), 305.1145.

Example 41

5-[4-(dimethylamino)phenyl]-3,3-dimethylindan-1-one

The title compound was prepared from trifluoro-methanesulfonic acid 3,3-dimethyl-1-oxo-indan-5-yl ester and 4-(dimethylamino)phenyl boronic acid according to the procedure described in example 21. MS m/z 280; HRMS: calcd for $C_{19}H_{21}NO+H^+$, 280.16959; found (ESI, [M+H]$^+$), 280.1691.

Example 42

5-[3-(dimethylamino)phenyl]-3,3-dimethylindan-1-one

The title compound was prepared from trifluoro-methanesulfonic acid 3,3-dimethyl-1-oxo-indan-5-yl ester and 3-(dimethylamino)phenyl boronic acid according to the procedure described in example 21. MS m/z 280; HRMS: calcd for $C_{19}H_{21}NO+H^+$, 280.16959; found (ESI, [M+H]$^+$), 280.1689.

Example 43

5-(3,4-difluorophenyl)-3,3-dimethylindan-1-one

The title compound was prepared from trifluoro-methanesulfonic acid 3,3-dimethyl-1-oxo-indan-5-yl ester and 3,4-difluorophenyl boronic acid according to the procedure described in example 21. MS m/z 273; HRMS: calcd for $C_{17}H_{14}F_2O+H^+$, 273.10855; found (ESI, [M+H]$^+$), 273.1078.

Example 44

5-[3-(ethylsulfonyl)phenyl]-3,3-dimethylindan-1-one

The title compound was prepared from trifluoro-methanesulfonic acid 3,3-dimethyl-1-oxo-indan-5-yl ester and 3-(ethylsulfonyl)phenyl boronic acid according to the procedure described in example 21. MS m/z 329; HRMS: calcd for $C_{19}H_{20}O_3S+H^+$, 329.12059; found (ESI, [M+H]$^+$), 329.1217.

Example 45

3-(3,3-dimethyl-1-oxo-2,3-dihydro-1H-inden-5-yl)-5-fluorobenzonitrile

The title compound was prepared from trifluoro-methanesulfonic acid 3,3-dimethyl-1-oxo-indan-5-yl ester and 3-cyano-5-fluorophenyl boronic acid according to the procedure described in example 21. MS (ES) m/z 280.1; HRMS: calcd for $C_{18}H_{14}FNO+H^+$, 280.11322; found (ESI, [M+H]$^+$), 280.1129.

Example 46

5-(4-acetylphenyl)-3,3-dimethylindan-1-one

The title compound was prepared from trifluoro-methanesulfonic acid 3,3-dimethyl-1-oxo-indan-5-yl ester and 4-acetylphenyl boronic acid according to the procedure described in example 21. MS (ES) m/z 279.2; HRMS: calcd for $C_{19}H_{18}O_2+H^+$, 279.13796; found (ESI, [M+H]$^+$), 279.1395.

Example 47

5-(3-acetylphenyl)-3,3-dimethylindan-1-one

The title compound was prepared from trifluoro-methanesulfonic acid 3,3-dimethyl-1-oxo-indan-5-yl ester and 3-acetyl phenyl boronic acid according to the procedure described in example 21. MS (ESI) m/z 279; HRMS: calcd for $C_{19}H_{18}O_2+H^+$, 279.13796; found (ESI, [M+H]$^+$), 279.1374.

Example 48

5-(2-acetylphenyl)-3,3-dimethylindan-1-one

The title compound was prepared from trifluoro-methanesulfonic acid 3,3-dimethyl-1-oxo-indan-5-yl ester and 2-acetylphenyl boronic acid according to the procedure described in example 21. MS (ESI) m/z 279; HRMS: calcd for $C_{19}H18O_2+H^+$, 279.13796; found (ESI, [M+H]$^+$), 279.1383.

Example 49

4-(3,3-dimethyl-1-oxo-2,3-dihydro-1H-inden-5-yl)benzonitrile

The title compound was prepared from trifluoro-methanesulfonic acid 3,3-dimethyl-1-oxo-indan-5-yl ester and 4-cyanophenyl boronic acid according to the procedure described in example 21. MS (ESI) m/z 262; HRMS: calcd for $C_{18}H_{15}NO+H^+$, 262.12264; found (ESI, [M+H]$^+$), 262.1237.

Example 50

3-(3,3-dimethyl-1-oxo-2,3-dihydro-1H-inden-5-yl)benzonitrile

The title compound was prepared from trifluoro-methanesulfonic acid 3,3-dimethyl-1-oxo-indan-5-yl ester and 3-cyanophenyl boronic acid according to the procedure described in example 21. MS (ESI) m/z 262; HRMS: calcd for $C_{18}H_{15}NO+H^+$, 262.12264; found (ESI, [M+H]$^+$), 262.1219.

Example 51

2-(3,3-dimethyl-1-oxo-2,3-dihydro-1H-inden-5-yl)benzonitrile

The title compound was prepared from trifluoro-methanesulfonic acid 3,3-dimethyl-1-oxo-indan-5-yl ester and 2-cyanophenyl boronic acid according to the procedure described in example 21. MS (ESI) m/z 262; HRMS: calcd for $C_{18}H_{15}NO+H^+$, 262.12264; found (ESI, [M+H]$^+$), 262.1234.

Example 52

Pharmacology

The compounds of this invention were tested in the relevant assay as described below and their potency are in the range of 0.01 nM to 5 μM in the in vitro assays and 0.001 to 300 mg/kg in the in vivo assays.

TABLE 1

Potency of representative 5-aryl-indan-1-one and analogs as PR modulators in progesterone induced T47D alkaline phosphatase assay

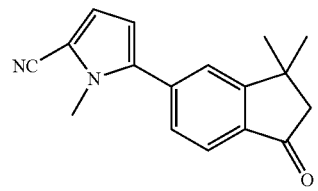

Example 3

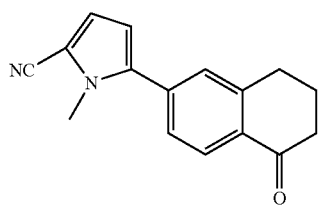

Example 13

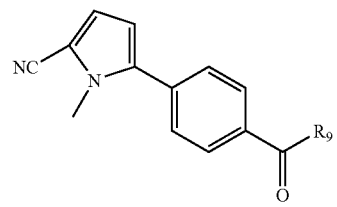

Examples 9–11

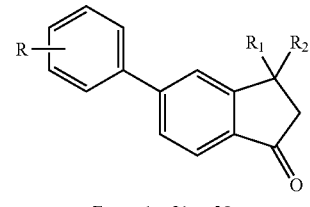

Examples 21 to 38

| Example No. | $R_1$ | $R_2$ | R | $R_9$ | Alk. Phos. IC$_{50}$ (nM) | Alk. Phos. EC$_{50}$ (nM) |
|---|---|---|---|---|---|---|
| 3 | Me | Me | — | — | — | 10 |
| 9 | — | H | — | Et | 115.2 | — |
| 10 | — | H | — | Thien-2-yl | 265.8 | — |
| 11 | — | H | — | Ph | 300 | — |
| 13 | H | H | — | — | 27.5 | — |
| 21 | Me | Me | 4-Cl | — | 199.5 | — |
| 26 | Me | Me | 4-Me | — | 877.1 | — |
| 28 | Me | Me | 3-Cl | — | 66.3 | — |
| 29 | Me | Me | 3-Me | — | 225.2 | — |
| 32 | Me | Me | 2-Cl | — | 737.3 | — |
| 35 | Me | Me | 2-Cl, 5-Cl | — | 631.5 | — |
| 36 | Me | Me | 2-Cl, 4-Cl | — | 349.1 | — |
| 37 | Me | Me | H | — | 300.4 | — |
| 38 | Me | Me | 3-Cl, 4-F | — | 100.4 | — |

(1) T47D Cell Proliferation Assay (a) Objective: Determination of progestational and anti-progestational potency by using a cell proliferation assay in T47D cells. A compound's effect on DNA synthesis in T47D cells is measured.

(b) Methods

A. Reagents

Growth medium: DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

Treatment medium: Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

B. Cell Culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hoursbefore treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hours.

C. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 minutes. The cells are rinsed three times with PBS and incubated with 3,3'5,5'-tetramethylbenzidine (TMB) substrate for 10-20 min depending upon the potency of tested compounds. Then 25 μL of 1 M sulfuric acid is added to each well to stop color reaction and optical density is read in a plate reader at 450 nm within 5 minutes.

(c) Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

(d) Reference Compounds:

Trimegestone and medroxyprogesterone acetate (MPA) were reference progestins and RU486 is the reference antiprogestin. All reference compounds were run in full dose-response curves and the $EC_{50}$ or $IC_{50}$ values were calculated.

TABLE 2

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |
| | 3 | 0.019 | 0.001 | 0.016 | 0.024 |
| MPA | 1 | 0.019 | 0.001 | 0.013 | 0.027 |
| | 2 | 0.017 | 0.001 | 0.011 | 0.024 |

TABLE 3

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
| | 2 | 0.016 | 0.001 | 0.014 | 0.020 |
| | 3 | 0.018 | 0.001 | 0.014 | 0.022 |

$EC_{50}$: Concentration of a compound that gives half-maximal increase in BrdU incorporation with SE;

$IC_{50}$: Concentration of a compound that gives half-maximal decrease in 0.1 trimegestone induced BrdU incorporation with SE (2) Rat Decidualization Assay (a) Objective: This procedure was used to evaluate the effect of progestins and antiprogestins on rat uterine decidualization and compare the relative potencies of various test compounds.

(b) Methods

A. Reagents

Test compounds were dissolved in 100% ethanol and mixed with corn oil (vehicle). Stock solutions of the test compounds in oil (Mazola™) were then prepared by heating (~80° C.) the mixture to evaporate ethanol. Test compounds were subsequently diluted with 100% corn oil or 10% ethanol in corn oil prior to the treatment of animals. No difference in decidual response was found when these two vehicles were compared.

B. Animals (RACUC protocol #5002)

Ovariectomized mature female Sprague-Dawley rats (~60-day old and 230 g) were obtained from Taconic (Taconic Farms, N.Y.) following surgery. Ovariectomy was performed at least 10 days prior to treatment to reduce circulating sex steroids. Animals were housed under 12 hourslight/dark cycle and given standard rat chow and water ad libitum.

C. Treatment

Rats were weighed and randomly assigned to groups of 4 or 5 before treatment. Test compounds in 0.2 mL vehicle were administered by subcutaneous injection in the nape of the neck or by gavage using 0.5 ml. The animals were treated once daily for seven days. For testing antiprogestins, animals were given the test compounds and a $EC_{50}$ dose of progesterone (5.6 mg/kg) during the first three days of treatment.

Following decidual stimulation, animals continued to receive progesterone until necropsy four days later.

D. Dosing

Doses were prepared based upon mg/kg mean group body weight. In all studies, a control group receiving vehicle was included. Determination of dose-response curves was carried out using doses with half log increases (e.g. 0.1, 0.3, 1.0, 3.0 mg/kg . . . ).

E. Decidual induction

Approximately 24 hoursafter the third injection, decidualization was induced in one of the uterine horns by scratching the antimesometrial luminal epithelium with a blunt 21 G needle. The contralateral horn was not scratched and served as an unstimulated control. Approximately 24 hoursfollowing the final treatment, rats were sacrificed by $CO_2$ asphyxiation and body weight measured. Uteri were removed and trimmed of fat. Decidualized (D-horn) and control (C-horn) uterine horns were weighed separately.

(c) Analysis of Results:

The increase in weight of the decidualized uterine horn was calculated by D-horn/C-horn and logarithmic transformation was used to maximize normality and homogeneity of variance. The Huber M-estimator was used to down weight the outlying transformed observations for both dose-response curve fitting and one-way analysis of variance. JMP software (SAS Institute, Inc.) was used for both one-way ANOVA and non-linear dose-response analyses.

(d) Reference Compounds: All progestin reference compounds were run in full dose-response curves and the $EC_{50}$ for uterine wet weight was calculated.

TABLE 4

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 5

Estimated average $EC_{50}$, standard error, and 95% confidence intervals for dose-response curves of 3 reference compounds

| Compound | $EC_{50}$ (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 6

Estimated $IC_{50}$, standard error, and 95% confident interval for the antiprogestin, RU 486

| Compound | Exp | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-kg)

C-horn: Wet weight of control uterine horn (default-kg)

Decidual response: $[(D-C)/C] \times 100\%$

Progestational activity: Compounds that induce decidualization significantly ($p<0.05$) compared to vehicle control are considered active Antiprogestational activity: Compounds that increase $EC_{50}$ progesterone induced decidualization significantly ($p<0.05$)

$EC_{50}$ for uterine weight: Concentration of compound that gives half-maximal decrease in $EC_{50}$ progesterone (default-mg/kg)

$IC_{50}$ for uterine weight: Concentration of compound that gives half-maximal decrease in $EC_{50}$ progesterone induced decidual response (default-mg/kg)

(3) PRE-Luciferase Assay in CV-1 Cells (a) Objective: To determine a compound's progestational or antiprogestational potency based on its effect on PRE-luciferase reporter activity in CV-1 cells co-transfected with human PR and PRE-luciferase plasmids.

(b) Methods

A. Reagents

Culture medium:

Growth medium: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL).

Experimental medium: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

B. Cell culture, transfection, treatment, and luciferase assay

Stock CV-1 cells were maintained in growth medium. Co-transfection was done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation was carried out at 260 V and 1,000 mF in a Biorad Gene Pulser II. After electroporation, cells were resuspended in growth medium and plated in 96-well plate at 40,000 cells/well in 200 μL. Following overnight incubation, the medium was changed to experimental medium. Cells were then treated with reference or test compounds in experimental medium. Compounds were tested for antiprogestational activity in the presence of 3 nM progesterone. Twenty-four hours after treatment, the medium was discarded, cells were washed three times with D-PBS (GIBCO, BRL). Fifty ml of cell lysis buffer (Promega, Madison, Wis.) was added to each well and the plates were shaken for 15 min in a Titer Plate Shaker (Lab Line Instrument, Inc.). Luciferase activity was measured using luciferase reagents from Promega.

(c) Analysis of Results

Each treatment consists of at least 4 replicates. Log transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear response analyses.

(d) Reference Compounds

Progesterone and trimegestone were reference progestins and RU486 was the reference antiprogestin. All reference compounds were run in full dose-response curves and the $EC_{50}$ or $IC_{50}$ values were calculated.

TABLE 7

Estimated $EC_{50}$, standard error (SE), and 95% confidence intervals (CI) for reference progestins from three individual studies

| Compound | Exp | $EC_{50}$ (nM) | SE | 95% CI lower | 95% CI upper |
|---|---|---|---|---|---|
| Progesterone | 1 | 0.616 | 0.026 | 0.509 | 0.746 |
| | 2 | 0.402 | 0.019 | 0.323 | 0.501 |
| | 3 | 0.486 | 0.028 | 0.371 | 0.637 |
| Trimegestone | 1 | 0.0075 | 0.0002 | 0.0066 | 0.0085 |
| | 2 | 0.0081 | 0.0003 | 0.0070 | 0.0094 |
| | 3 | 0.0067 | 0.0003 | 0.0055 | 0.0082 |

TABLE 8

Estimated $IC_{50}$, standard error (SE), and 95% confident interval (CI) for the antiprogestin, RU486 from three individual studies

| Compound | Exp | $IC_{50}$ (nM) | SE | 95% CI lower | 95% CI upper |
|---|---|---|---|---|---|
| RU 486 | 1 | 0.028 | 0.002 | 0.019 | 0.042 |
| | 2 | 0.037 | 0.002 | 0.029 | 0.048 |
| | 3 | 0.019 | 0.001 | 0.013 | 0.027 |

Progestational activity: Compounds that increase PRE-luciferase activity significantly ($p<0.05$) compared to vehicle control are considered active.

Antiprogestational activity: Compounds that decrease 3 nM progesterone induced PRE-luciferase activity significantly ($p<0.05$).

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

(4) T47D Cell Alkaline Phosphatase Assay (a) Purpose: To identify progestins or antiprogestins by determining a compound's effect on alkaline phosphatase activity in T47D cells.

(b) Methods

A. Reagents

Culture medium: DMEM:F12 (1:1) (GIBCO, BRL) supplemented with 5% (v/v) charcoal stripped fetal bovine serum (not heat-inactivated), 100 U/ml penicillin, 100 mg/ml streptomycin, and 2 mM GlutaMax (GIBCO, BRL).

Alkaline phosphatase assay buffer:

I. 0.1 M Tris-HCl, pH 9.8, containing 0.2% Triton X-100

II. 0.1 M Tris-HCl, pH 9.8 containing 4 mM p-nitrophenyl phosphate (Sigma).

B. Cell Culture and Treatment

Frozen T47D cells were thawed in a 37° C. water bath and diluted to 280,000 cells/ml in culture medium. To each well in a 96-well plate (Falcon, Becton Dickinson Labware), 180 μL of diluted cell suspension was added. Twenty μL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$ humidified atmosphere for 24 hours.

Note: For high throughput screening, one concentration of each compound was tested at 0.3 mg/ml. Based on an average molecular weight of 300 g/mol for the compounds in the library, the concentration was approximately 1 mM. Subsequently, active compounds were tested in dose response assays to determine $EC_{50}$ or $IC_{50}$.

C. Alkaline Phosphatase Enzyme Assay

At the end of treatment, the medium was removed from the plate. Fifty μL of assay buffer I was added to each well. The plates were shaken in a titer plate shaker for 15 minutes. Then 150 μL of assay buffer II was added to each well. Optical density measurements were taken at 5 min intervals for 30 min at a test wavelength of 405 nM.

(c) Analysis of Results

Analysis of dose-response data: For reference and test compounds, a dose response curve was generated for dose (X-axis) vs. the rate of enzyme reaction (slope) (Y-axis). Square root-transformed data were used for analysis of variance and nonlinear dose response curve fitting for both agonist and antagonist modes. Huber weighting was used to downweight the effects of outliers. $EC_{50}$ or $IC_{50}$ values were calculated from the retransformed values. JMP software (SAS Institute, Inc.) was used for both one-way analysis of variance and non-linear dose response analyses in both single dose and dose response studies.

(d) Reference Compounds:

Progesterone and trimegestone were reference progestins and RU486 was the reference antiprogestin. All reference compounds were run in full dose response curves and the $EC_{50}$ or $IC_{50}$ values were calculated.

TABLE 9

Estimated $EC_{50}$, standard error (SE), and 95% confidence intervals (CI) for reference progestins from three independent experiments

| Compound | Exp | $EC_{50}$ (nM) | SE | 95% CI lower | 95% CI upper |
|---|---|---|---|---|---|
| Progesterone | 1 | 0.839 | 0.030 | 0.706 | 0.996 |
| | 2 | 0.639 | 0.006 | 0.611 | 0.669 |
| | 3 | 1.286 | 0.029 | 1.158 | 1.429 |
| Trimegestone | 1 | 0.084 | 0.002 | 0.076 | 0.091 |
| | 2 | 0.076 | 0.001 | 0.072 | 0.080 |
| | 3 | 0.160 | 0.004 | 0.141 | 0.181 |

TABLE 10

Estimated $IC_{50}$ standard error, and 95% confident interval for the reference antiprogestin RU486 from three independent experiments

| Compound | Exp | $IC_{50}$ (nM) | SE | 95% CI lower | 95% CI upper |
|---|---|---|---|---|---|
| RU 486 | 1 | 0.103 | 0.002 | 0.092 | 0.115 |
| | 2 | 0.120 | 0.001 | 0.115 | 0.126 |
| | 3 | 0.094 | 0.007 | 0.066 | 0.134 |

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of formula II:

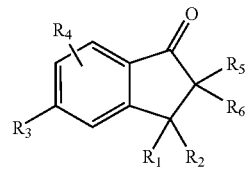

wherein:
$R_1$ and $R_2$ are, independently, selected from the group consisting of H, halogen, $C_1$ to $C_6$ alkyl, $CF_3$, $CF_2CF_3$, $C_2$ to $C_6$ alkenyl, $C_2$ to $C_6$ alkynyl, $C_3$ to $C_8$ cycloalkyl, aryl, and substituted aryl;
provided that both $R_1$ and $R_2$ are not H; or
$R_1$ and $R_2$ are fused to form (a) or (b):
  (a) a carbon-based 3 to 6 membered saturated spirocyclic ring; or
  (b) a carbon-based 3 to 6 membered spirocyclic ring having in its backbone one or more carbon-carbon double bonds;
  wherein rings (a)-(b) are optionally substituted by 1 to 3 substituents selected from the group consisting of F, Cl, and $C_1$ to $C_3$ alkyl;
$R_3$ is a saturated 5 membered heteroaryl ring containing in its backbone 1 to 3 heteroatoms selected from the group consisting of O, S, SO, $SO_2$, and $NR^C$ and substituted with 0 to 3 substituents selected from the group consisting of H, halogen, CN, $NO_2$, OH, amino, $C_1$ to $C_4$ alkyl, $C_1$ to $C_4$ alkoxy, $C_1$ to $C_4$ alkylamino, C=$NOR^C$, $COR^D$, and $NR^C COR^D$; or
$R^C$ is absent, H, $C_1$ to $C_4$ alkyl, substituted $C_1$ to $C_4$ alkyl, CN, or $COR^D$;
$R^D$ is H, $C_1$ to $C_4$ alkyl, $C_1$ to $C_4$ alkoxy, or $C_1$ to $C_4$ alkylamino;
$R_4$ is H, halogen, CN, OH, $NO_2$, alkoxy, or lower alkyl;
$R_5$ and $R_6$ are, independently, H, F, or $C_1$ to $C_3$ alkyl;
or a pharmaceutically acceptable salt thereof.

2. The compound according to claim 1, wherein:
$R_1$ and $R_2$ are fused to form (a) or (b).

3. A pharmaceutical composition comprising a compound of claim 1 or a pharmaceutically acceptable salt thereof, and a pharmaceutically acceptable carrier or excipient.

* * * * *

UNITED STATES PATENT AND TRADEMARK OFFICE
CERTIFICATE OF CORRECTION

PATENT NO. : 7,319,152 B2 Page 1 of 1
APPLICATION NO. : 11/522862
DATED : January 15, 2008
INVENTOR(S) : Zhang et al.

It is certified that error appears in the above-identified patent and that said Letters Patent is hereby corrected as shown below:

(1)  Col. 10, line 9, replace "Scheme I" with -- Scheme III --.

Signed and Sealed this

Twenty-fourth Day of June, 2008

JON W. DUDAS
*Director of the United States Patent and Trademark Office*